United States Patent
Venetianer et al.

(10) Patent No.: US 10,095,930 B2
(45) Date of Patent: Oct. 9, 2018

(54) SYSTEM AND METHOD FOR HOME HEALTH CARE MONITORING

(71) Applicant: Avigilon Fortress Corporation, Vancouver (CA)

(72) Inventors: Peter L. Venetianer, McLean, VA (US); Gary W. Myers, Aldie, VA (US); Zhong Zhang, Great Falls, VA (US)

(73) Assignee: AVIGILON FORTRESS CORPORATION, Vancouver, British Columbia (CA)

( * ) Notice: Subject to any disclaimer, the term of this patent is extended or adjusted under 35 U.S.C. 154(b) by 0 days.

(21) Appl. No.: 15/150,456

(22) Filed: May 10, 2016

(65) Prior Publication Data
US 2016/0253802 A1    Sep. 1, 2016

Related U.S. Application Data

(63) Continuation of application No. 13/744,266, filed on Jan. 17, 2013, now Pat. No. 9,338,409.

(Continued)

(51) Int. Cl.
*G06K 9/00* (2006.01)
*H04N 7/18* (2006.01)
(Continued)

(52) U.S. Cl.
CPC ........ *G06K 9/00718* (2013.01); *A61B 5/0013* (2013.01); *A61B 5/0046* (2013.01);
(Continued)

(58) Field of Classification Search
CPC ........... G06K 9/00771; G06K 9/00369; G06K 9/00711; G06K 9/00335; G06K 9/00744;
(Continued)

(56) References Cited

U.S. PATENT DOCUMENTS

| 5,544,649 A | 8/1996 | David et al. |
| 5,553,609 A | 9/1996 | Chen et al. |

(Continued)

FOREIGN PATENT DOCUMENTS

| KR | 10-0234196 B1 | 12/1999 |
| WO | WO 2012/037157 A2 | 3/2012 |

*Primary Examiner* — Amara Abdi
(74) *Attorney, Agent, or Firm* — Muir Patent Law, PLLC

(57) ABSTRACT

A monitoring method and system are disclosed. In one embodiment, a method includes monitoring the health of a person in a home. The method includes capturing a video sequence from a first camera disposed within the home, including capturing two-dimensional image data for the video sequence; receiving depth data corresponding to the two-dimensional data, and associating the depth data with the video sequence as metadata; setting a plurality of events to monitor associated with the person, the events defined to include actions captured from the first camera, at least a first event including the person's body being in a particular bodily position and performing video content analysis on the video sequence to determine whether the events have occurred. The video content analysis includes automatically detecting a potential human object from the video sequence based on the two-dimensional image data; using the depth data to determine a size and bodily position of the potential human object; and based on the size of the potential object, confirming that the potential human object is an actual human, thereby confirming the potential human object as a target. The method further includes determining that the first event has occurred based on the determined bodily position of the target.

14 Claims, 19 Drawing Sheets

Related U.S. Application Data

(60) Provisional application No. 61/587,186, filed on Jan. 17, 2012.

(51) Int. Cl.

| | | |
|---|---|---|
| *A61B 5/00* | (2006.01) | |
| *A61B 5/107* | (2006.01) | |
| *A61B 5/11* | (2006.01) | |
| *A61B 5/1171* | (2016.01) | |
| *G08B 13/196* | (2006.01) | |
| *G08B 21/04* | (2006.01) | |
| *G06T 7/00* | (2017.01) | |
| *G06T 7/73* | (2017.01) | |
| *G06T 7/50* | (2017.01) | |
| *G06T 7/55* | (2017.01) | |
| *G06T 7/579* | (2017.01) | |
| *G06T 7/246* | (2017.01) | |
| *G06T 7/62* | (2017.01) | |

(52) U.S. Cl.
CPC .......... *A61B 5/0077* (2013.01); *A61B 5/1072* (2013.01); *A61B 5/1073* (2013.01); *A61B 5/1079* (2013.01); *A61B 5/1113* (2013.01); *A61B 5/1116* (2013.01); *A61B 5/1117* (2013.01); *A61B 5/1128* (2013.01); *A61B 5/1176* (2013.01); *A61B 5/7282* (2013.01); *A61B 5/746* (2013.01); *G06K 9/00087* (2013.01); *G06K 9/00369* (2013.01); *G06K 9/00771* (2013.01); *G06T 7/0016* (2013.01); *G06T 7/246* (2017.01); *G06T 7/50* (2017.01); *G06T 7/55* (2017.01); *G06T 7/579* (2017.01); *G06T 7/62* (2017.01); *G06T 7/73* (2017.01); *G08B 13/19615* (2013.01); *G08B 21/043* (2013.01); *G08B 21/0476* (2013.01); *H04N 7/18* (2013.01); *H04N 7/181* (2013.01); *A61B 2505/07* (2013.01); *G06K 2009/00738* (2013.01); *G06T 2207/10016* (2013.01); *G06T 2207/30196* (2013.01); *G06T 2207/30232* (2013.01)

(58) Field of Classification Search
CPC .......... G06K 9/00362; G06K 9/00087; G06K 9/00718; G06K 2009/00738; G06T 2207/10016; G06T 7/20; G06T 2207/30196; G06T 2207/30232; G06T 7/0081; G06T 2207/30244; G06T 7/2093; G06T 7/0016; G06T 7/246; G06T 7/50; G06T 7/55; G06T 7/579; G06T 7/62; G06T 7/73; A61B 5/0013; A61B 5/0046; A61B 5/0077; A61B 5/1072; A61B 5/1073; A61B 5/1079; A61B 5/1113; A61B 5/1116; A61B 5/1117; A61B 5/1128; A61B 5/1176; A61B 5/7282; A61B 5/746; A61B 2505/07; G08B 13/19615; G08B 21/043; G08B 21/0476; H04N 7/18; H04N 7/181
See application file for complete search history.

(56) References Cited

U.S. PATENT DOCUMENTS

| | | |
|---|---|---|
| 6,792,319 B1 | 9/2004 | Bilger |
| 7,516,888 B1 | 4/2009 | Kundu et al. |
| 7,551,770 B2 * | 6/2009 | Harman ............... G06T 9/001 382/154 |
| 7,801,330 B2 | 9/2010 | Zhang et al. |
| 7,825,954 B2 | 11/2010 | Zhang et al. |
| 7,831,087 B2 | 11/2010 | Harville |
| 7,868,912 B2 | 1/2011 | Venetainer et al. |
| 7,932,923 B2 | 4/2011 | Lipton et al. |
| 8,233,660 B2 | 7/2012 | Fritch et al. |
| 8,238,607 B2 | 8/2012 | Wang et al. |
| 8,320,621 B2 | 11/2012 | McEldowney |
| 2003/0034971 A1 | 2/2003 | Fujiwara et al. |
| 2004/0153671 A1 | 8/2004 | Schuyler et al. |
| 2005/0201612 A1 | 9/2005 | Park et al. |
| 2007/0070190 A1 * | 3/2007 | Yin ............... G08B 13/19626 348/36 |
| 2007/0127774 A1 | 6/2007 | Zhang et al. |
| 2008/0021731 A1 | 1/2008 | Rodgers |
| 2009/0063307 A1 | 3/2009 | Groenovelt et al. |
| 2009/0080711 A1 | 3/2009 | Yokoi |
| 2009/0281392 A1 | 11/2009 | Brown |
| 2010/0197393 A1 | 8/2010 | Geiss |
| 2010/0199228 A1 | 8/2010 | Latta et al. |
| 2011/0080336 A1 * | 4/2011 | Leyvand ............... G06K 9/469 345/156 |
| 2011/0034109 A1 | 6/2011 | Izumi |
| 2011/0134109 A1 | 6/2011 | Izumi |
| 2011/0143779 A1 | 6/2011 | Rowe et al. |
| 2011/0200229 A1 | 8/2011 | Tuzel et al. |
| 2011/0285910 A1 | 11/2011 | Bamji et al. |
| 2012/0020518 A1 | 1/2012 | Taguchi |
| 2012/0025989 A1 | 2/2012 | Cuddihy et al. |
| 2012/0026289 A1 | 2/2012 | Suenaga et al. |
| 2012/0026308 A1 | 2/2012 | Johnson et al. |
| 2012/0075464 A1 * | 3/2012 | Derenne ............... A61B 5/0013 348/135 |
| 2012/0087572 A1 * | 4/2012 | Dedeoglu ............. G06K 9/00771 382/154 |
| 2012/0087573 A1 | 4/2012 | Sharma et al. |
| 2012/0140068 A1 | 6/2012 | Monroe et al. |
| 2012/0293635 A1 | 11/2012 | Sharma et al. |
| 2012/0314905 A1 | 12/2012 | Wang et al. |
| 2013/0041290 A1 * | 2/2013 | Kording ............... A61B 5/1101 600/595 |
| 2013/0073093 A1 | 3/2013 | Songkakul |
| 2013/0182114 A1 | 7/2013 | Zhang et al. |
| 2013/0182905 A1 | 7/2013 | Myers et al. |
| 2013/0184592 A1 | 7/2013 | Zhang et al. |
| 2013/0184887 A1 | 7/2013 | Ainsley et al. |

\* cited by examiner

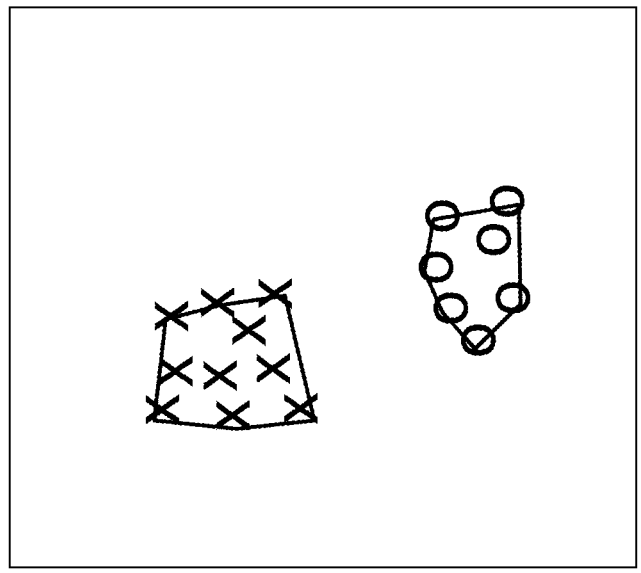
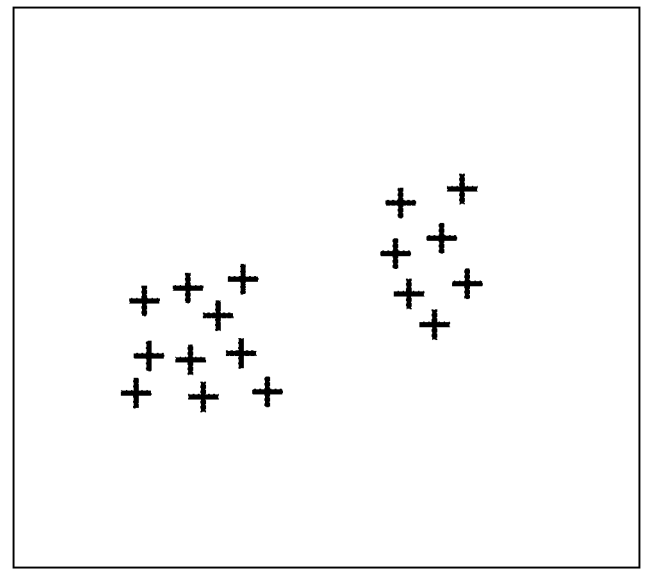

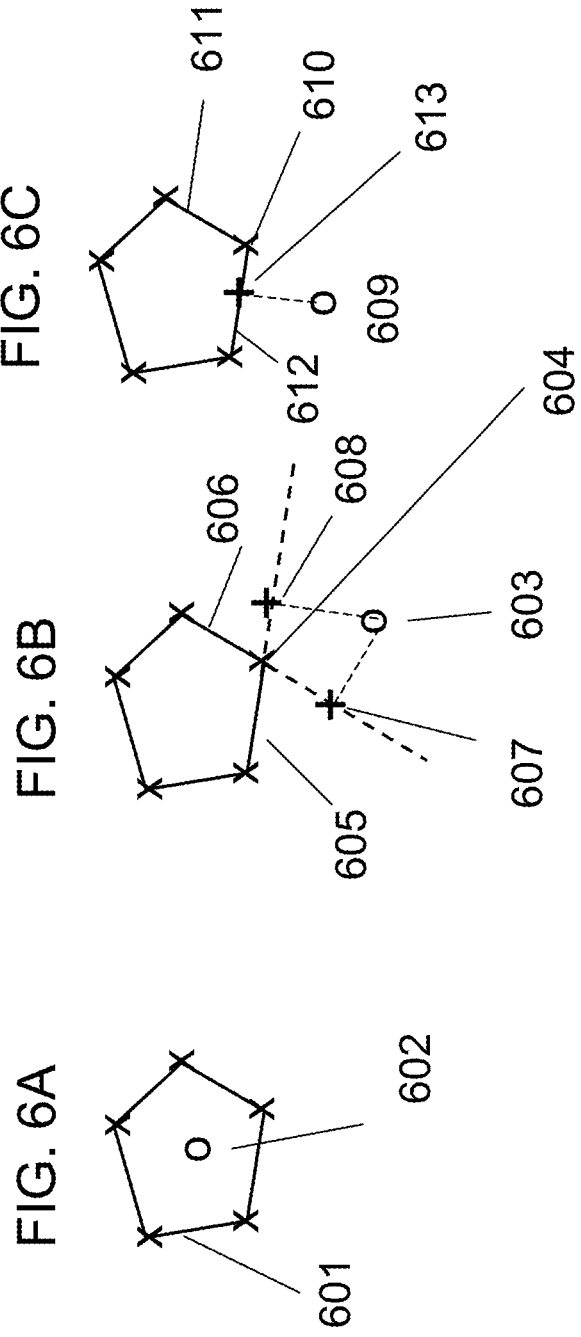

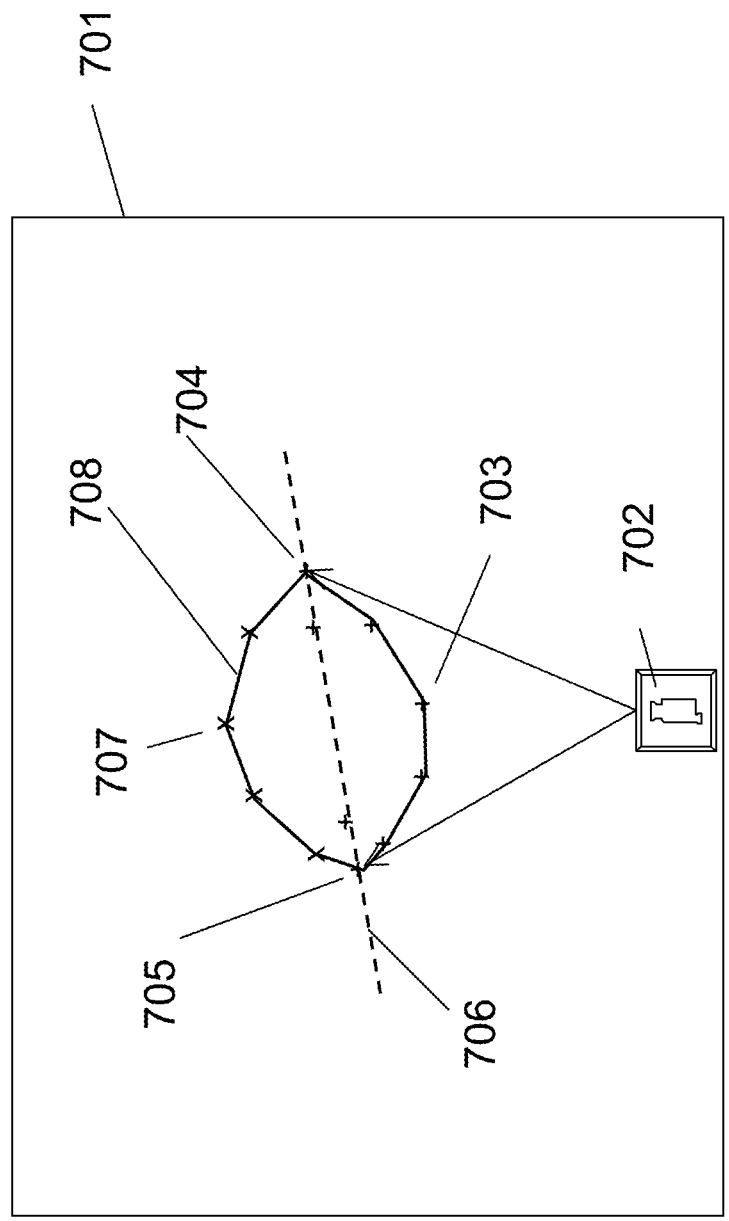

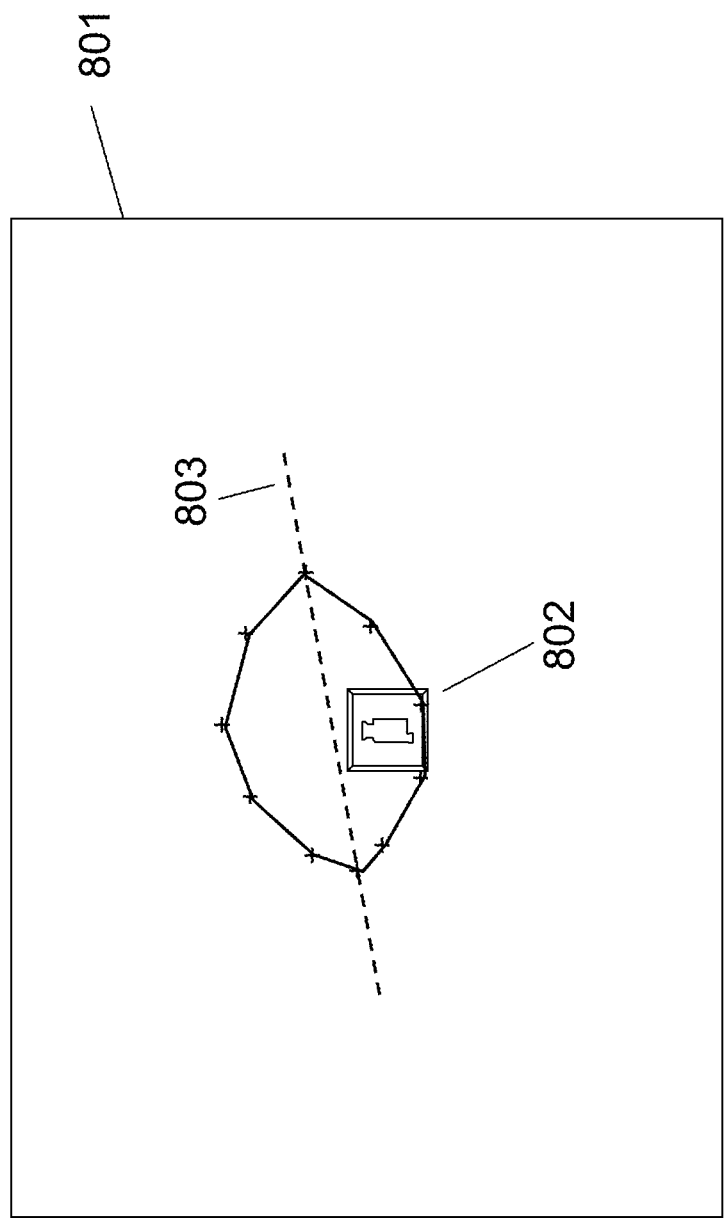

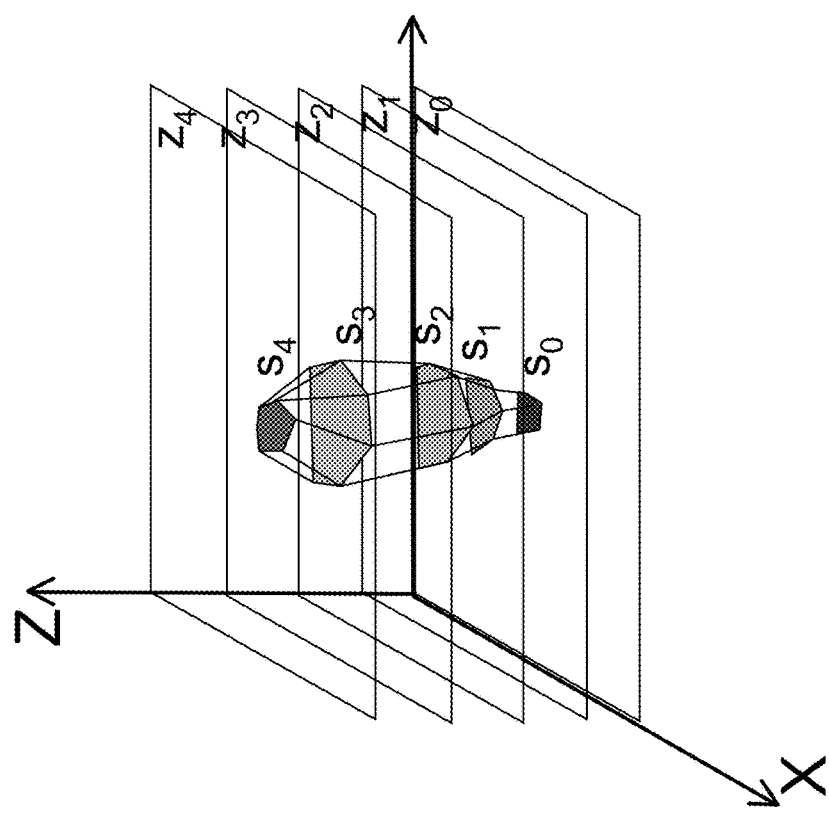

SYSTEM AND METHOD FOR HOME HEALTH CARE MONITORING

CROSS-REFERENCE TO RELATED APPLICATION

This application is a continuation application of U.S. patent application Ser. No. 13/744,266, filed Jan. 17, 2013, and now U.S. Pat. No. 9,338,409, issued on May 10, 2016, which claims the benefit of priority to U.S. Provisional Patent Application No. 61/587,186, filed Jan. 17, 2012, the contents of each of which are incorporated herein by reference in their entirety.

BACKGROUND

1. Field

This disclosure relates to a system for performing home health care monitoring. More specifically, this disclosure relates to a system for performing home health care monitoring using depth-enhanced video content analysis.

2. Background

Many people, particularly the elderly, need to take certain medications and maintain a certain level of physical activity to stay healthy. In addition, as people get older, there tends to be a greater likelihood of accidents or sudden emergencies, such as falling down, stroke, heart attacks, emergencies due to a failure to take medicine, etc. In addition, many elderly people suffer from depression, dementia, or other conditions that alter their daily behavior. Preventing and treating these accidents, emergencies, and conditions is very important but can be very expensive. For example, people may move into assisted living quarters or nursing homes, or may hire hospice care or home help.

To assist elderly patients, various less expensive alternatives have been used. For example, using Lifeline® by Philips, elderly patients can simply push a button if an emergency situation occurs, which alerts emergency response personnel. Other systems may use video or other electrical equipment to monitor a patient's health. For example, U.S. Pat. No. 5,544,649 to David et al., published on Aug. 13, 1996, describes a patient health monitoring system that includes video cameras in a person's home that connect to a central station for health care workers to monitor. Additional medical condition sensing and monitoring equipment, such as blood pressure, pulse, and temperature monitoring devices, may also be used at the patient's home. However, such a system uses a fairly large number of health care workers per patient, and therefore can still be fairly expensive and requires constant attention of the workers.

In hospital environments, cameras that perform automatic detection of certain patient behaviors have been proposed. For example, U.S. Patent Application Publication No. 2012/0075464 to Derenne et al., published on Mar. 29, 2012, proposes the use of video cameras in the hospital environment to determine certain patient conditions, such as whether a patient is sleeping, exiting a bed, walking, or falling. Proposed cameras for such a system include RGB cameras with depth sensors that may be used to provide full-body 3D motion detection, among other things.

However, systems such as proposed by Derenne et al., while monitoring individual events, do not monitor collective household activity such as to be expected of an elderly patient living at home. In addition, systems that provide full 3D motion detection, for example by analyzing three-dimensional data for all parts of a video scene (e.g., all pixels of a series of video frames) can be computationally complex, and may require special software and processing capability beyond the scope of traditional two-dimensional monitoring schemes, which may further increase the expense of such monitoring.

An example of a two-dimensional video content analysis (VCA) system is described in U.S. Pat. No. 7,932,923, issued to Lipton et al. on Apr. 26, 2011 (the '923 patent), the contents of which are incorporated herein by reference in their entirety. Some existing systems use RGB (red green blue), CMYK (cyan magenta yellow key), YCbCr, or other sensors that sense images in a two-dimensional manner and perform analysis of those images to perform object and event detection. Other existing systems use depth sensors, to generate three-dimensional data or depth maps, which are then analyzed using different software in order to perform object and event detection. In some ways, the systems that use depth sensors are more accurate than the two-dimensional systems. For example, the depth sensor systems may obtain more accurate three-dimensional information, and may deal better with occlusions. However, depth data and images determined by depth sensor systems are generally lower in resolution than RGB data, and may therefore include fewer details than RGB images. In addition, depth sensors are a relatively new technology for video analysis, and are still prone to error in determining three-dimensional coordinates. Further, certain information resulting from depth sensors often remains incomplete, such as depth information for objects with specularities, or depth information for featureless surfaces extracted from stereo.

Certain systems may combine both depth and RGB data in order to perform analysis on complex three-dimensional scenes. For example, as described in U.S. Pat. No. 7,831,087, depth data and optional non-depth data are used to generate a plan-view image, which plan view image can then be analyzed by classifying objects in the plan view image. However, systems such as this, which perform complex analysis on depth data and optional additional data in order to perform object detection or event detection, still suffer from the problems above relating the drawbacks of depth sensor systems. For example, some of the depth data may be missing or may be inaccurate, resulting in an analysis of faulty data. In addition, performing analysis on three-dimensional data generally requires more complex algorithms and may require a complete re-design of hardware and/or software that performs the analysis, compared to more traditional two-dimensional image analysis systems.

The embodiments described here address some of these problems of existing systems, and provide a new and simplified way to use depth data to assist in image analysis and video content analysis throughout a patient home environment. As a result, better home health care monitoring can be achieved using automated systems that are more accurate and reliable than prior systems.

SUMMARY

The disclosed embodiments include a home health care monitoring system. The system includes a plurality of sensors throughout a patient's home, and performs depth-enhanced video content analysis on a plurality of video sequences captured by the plurality of cameras. In certain embodiments, the system performs initial video content analysis steps, such as object detection, on two-dimensional image data captured by the cameras. The system then performs additional analysis on the detected objects using depth data captured by the cameras. For example, the object detection may detect a human in a video frame, and the depth data may then be used to determine and/or confirm whether the human is lying down, sitting, or standing. Based on this process, information such as how long a patient is sitting, standing, and lying down throughout the home, or how often a patient visits certain rooms can be determined, and such information can be used to assist in monitoring the patient's health.

BRIEF DESCRIPTION OF THE DRAWINGS

Example embodiments will be more clearly understood from the following detailed description taken in conjunction with the accompanying drawings. The figures represent non-limiting example embodiments as described herein.

FIGS. 5A-5B show examples of two separate groups of pixels in a Z-plane, according to certain exemplary embodiments.

FIGS. 6A-6C show exemplary methods of computing the distance between a pixel and convex null, according to certain embodiments.

FIG. 7 shows a method of determining a blob convex hull on a Z-plane for one camera location, according to certain exemplary embodiments.

FIG. 8 shows another example of determining a blob convex hull on a Z-plane for another camera location, according to certain exemplary embodiments.

FIG. 9 depicts an example of an image blob and its projected convex hull slices on a list of corresponding Z-planes, according to one exemplary embodiment.

DETAILED DESCRIPTION

Figure 1:
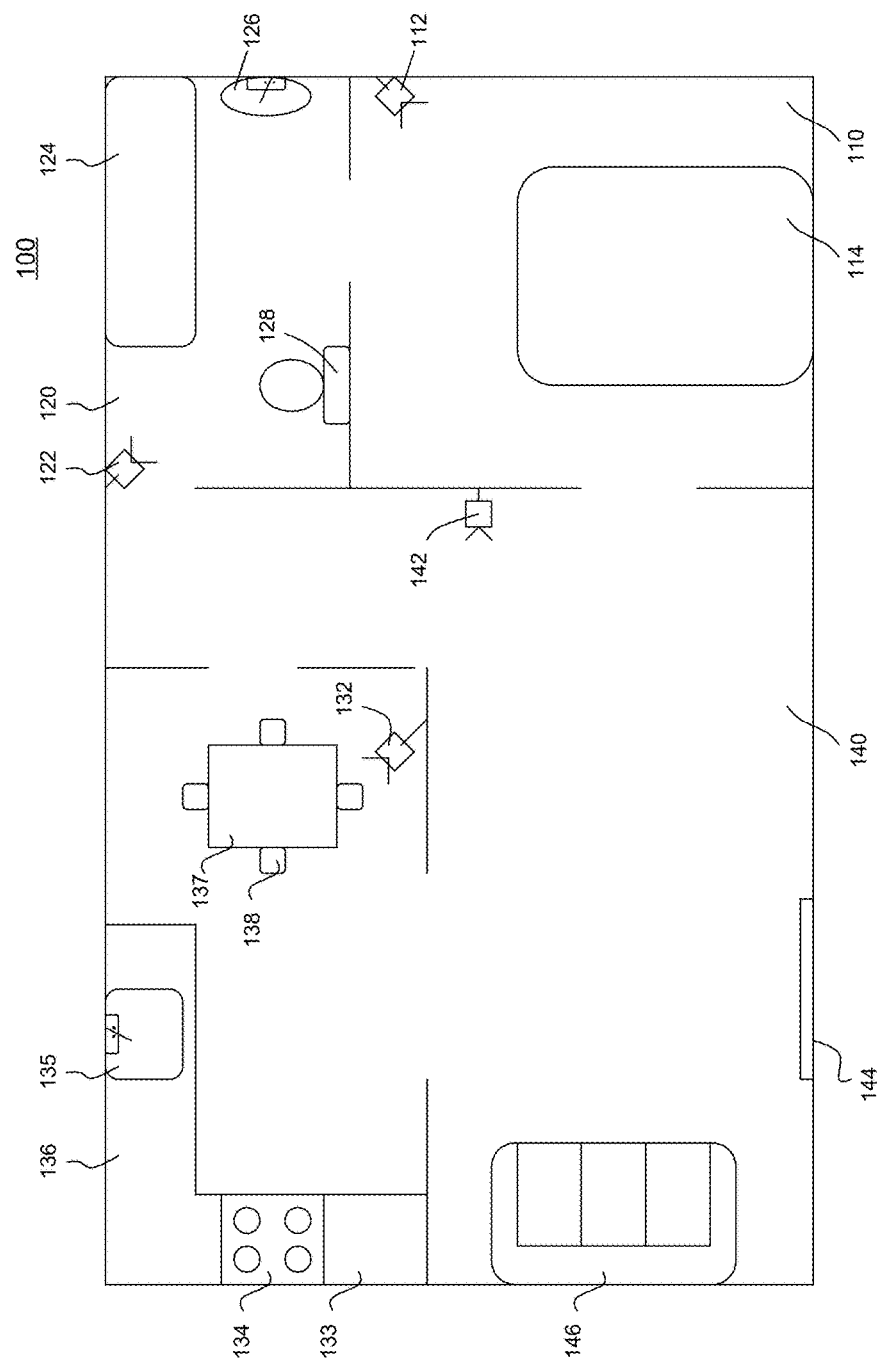
FIG. 1 shows an exemplary home environment including a home health care monitoring system, according to certain exemplary embodiments.

The present disclosure will be described more fully hereinafter with reference to the accompanying drawings, in which various embodiments are shown. The invention may, however, be embodied in many different forms and should not be construed as limited to the embodiments set forth herein. In the drawings, like numbers refer to like elements throughout.

It will be understood that when an element is referred to as being "connected" or "coupled" to or "in communication with" another element, it can be directly connected or coupled to or in communication with the other element or intervening elements may be present. In contrast, when an element is referred to as being "directly connected" or "directly coupled" or "in direct communication with" another element, there are no intervening elements present. As used herein, the term "and/or" includes any and all combinations of one or more of the associated listed items and may be abbreviated as "/".

It will be understood that, although the terms first, second, etc. may be used herein to describe various elements, these elements should not be limited by these terms. Unless indicated otherwise, these terms are only used to distinguish one element from another. For example, a first signal could be termed a second signal, and, similarly, a second signal could be termed a first signal without departing from the teachings of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

This disclosure includes particular terminology and descriptions that relate to home health care, video surveillance, and video content analysis. The descriptions are intended to provide a framework for certain terms and concepts, and are not intended to limit the scope of this disclosure unless explicitly stated.

FIG. 1 depicts an exemplary dwelling 100 in which a home health care monitoring system may be used. As shown in FIG. 1, dwelling 100 includes a plurality of rooms and a plurality of cameras. For example, dwelling 100 includes a bedroom 110 including camera 112, and bed 114; bathroom 120 including camera 122, bath 124, sink 126, and toilet 128; kitchen/dining room including camera 132, refrigerator 133, stove 134, sink 135, counter 136, table 137, and chairs 138; and living room 140 including camera 142, front door 144, and couch 146. Although one camera is shown in each room, additional setups are possible. For example, certain rooms may have no cameras, and others may include a plurality of cameras.

In one embodiment, cameras such as 112, 122, 132, and 142 may be positioned to capture video frames likely to relate to events of interest for home health care monitoring. For example, if the amount of time sitting, standing, and lying down is to be monitored, then cameras may be positioned to capture video of the bed 114 (e.g., camera 112), the kitchen chairs 138 (e.g., camera 132), and the couch 146 (e.g., camera 142). As another example, if a number of times entering a kitchen or bathroom is to be monitored, then kitchen camera 132 and bathroom camera 122 may be positioned to capture video of the entranceways to the kitchen and bathroom. As yet another embodiment, if the taking of oral medication is to be monitored, then both the bathroom camera 122 and the kitchen camera 132 may be positioned to capture video of the respective sinks 126, 135, or the counter spaces.

As described further below, a video surveillance system (e.g., including cameras 112, 122, 132, and 142) can use depth data to assist in monitoring home health care in a patient's home. For example, video sequences from multiple devices in different rooms can be collectively analyzed to detect certain behaviors and monitor overall behavioral patterns of a patient at home. These sequences can be analyzed by a central computing system in the home, and/or by a remote computing system (e.g., connected via a telecommunications medium and over a network such as the Internet). Alternatively or additionally, some or all of the depth enhanced video sequences can be analyzed by the cameras that capture them. Events can be monitored, and as a result, alerts can be configured to warn the patient, a monitoring service, or outside professionals that an event occurred. For example, alerts can be sent to a health care professional via e-mail, phone, or other audio-visual means, and the alerts can include a snapshot or video clip or live feed of video from a camera in the patient's home. In one embodiment, an alerted professional can request a live audio or video communication with the patient prior to communicating. To address privacy concerns, in one embodiment, a video of the patient is only sent if the patient gives permission, or if an emergency alert is issued.

In one embodiment, each of the video cameras/depth sensors 112, 122, 132, 142 may be networked or otherwise in communication (e.g., hard wired or wirelessly) with a server (not shown). Each video camera may include a processor to perform video content analysis of the corresponding video images taken. The content analysis may analyze the two dimensional video image data with the depth information provided by the depth sensor associated with the video camera, and may also analyze the two dimensional video image data alone. On camera processors of each video camera may perform such content analysis to generate video primitives, also referred to herein as metadata, and stream the video primitives/metadata to the server. The video primitives/metadata may represent detected objects, detected classification and/or characteristics of the detected objects and/or actions and/or events (e.g., of the detected objects) detected in the corresponding video. The video primitives, or metadata, may be associated with each frame of the video sequence. By way of example, see U.S. Pat. No. 7,868,912 issued to Venetianer et al. and U.S. Pat. No. 7,932,923 issued to Lipton et al., both of which are incorporated herein by reference in their entirety, for exemplary details of video primitive (or metadata) generation and downstream processing (which may be real time processing or later processing) to obtain information from the video, such as event detection, using the generated video primitives. Depth data associated with the video image data may be provided to the server as metadata along with other metadata. Alternatively and/or in addition, height data derived from the depth data (e.g., from on camera processing) may be provided to the server as metadata along with other metadata. The depth metadata and/or height metadata may be associated with detected objects and may include depth and/or height of multiple elements of the detected object. The depth and/or height data and other metadata obtained from on camera processing of the video image data of the corresponding video camera may be streamed to the server.

Alternatively, the video camera/depth sensors 112, 122, 132, 142 may provide recorded video and associated depth data to the server or another computer without processing. In this example, each camera may stream to a server or to another computer the video image data together with the depth data. The server or the other computer may then process the video image data and depth data provided by the video cameras/depth sensors 112, 122, 132, 142. Such processing may also generate metadata derived from the video image data and depth metadata and/or height metadata as described previously.

The metadata may be processed to classify objects, and to detect actions and events without reprocessing the original video image data. Upon detecting an action/event of interest, the original video image data may be accessed by a user to verify the action/event detection or to review for other purposes.

As described in greater detail below, depth data added to a two-dimensional analysis can be used to detect various types of events. Further events can be based on an individual episode, or a collection of episodes involving the patient throughout the house. As an example, using the two-dimensional data and depth data, a home health care monitoring system can first use conventional two-dimensional processing to determine, for example that the patient is in a particular room. Then, using depth data, the system can determine a height of the patient in order to determine whether the person is standing, sitting, or lying down. That information can be monitored over time, in order to develop a behavioral profile indicating how often the person is lying down, sitting, and/or standing throughout a day and throughout the house.

As another example, events such as a patient falling down, getting out of bed, or staying in bed too long can be more accurately determined using depth data in combination with two-dimensional image data, also referred to as depth-enhanced video data in a video monitoring system. For example, in a traditional two-dimensional monitoring system, a person can be detected using, for example, face recognition or body shape recognition. However, the system may still have trouble determining if the person is standing, sitting up, or lying down. Therefore, the various embodiments discussed herein can better determine whether a person is standing up or lying down, or whether a person has recently fallen down, by using the depth data in combination with two-dimensional image data.

In other embodiments, based on information collected throughout a day, for example, the monitoring system can determine how many times a patient visited different rooms or performed different activities. For example, a count of bathroom visits or kitchen visits can be used to determine if the patient is exhibiting normal healthy behavior (e.g., if the person is eating enough). A determination of how many times a patient took medicine can also be used to determine if the patient is following recommended healthy patterns. Also, to assist the patient and prevent the patient from falling, the monitoring system can be integrated with a lighting system, in order to turn lights automatically on or off depending on whether a person has woken up, fallen asleep, gotten out of bed, etc.

In addition, in situations where a patient is occluded by one or more objects (e.g., a bedpost, a kitchen table, a pet, etc.), by using the depth data, a more accurate monitoring of the patient can be performed.

In order to appreciate the advantages of using a depth sensing system for home health care, a detailed discussion of certain existing video content analysis systems, as well a combined two-dimensional and depth sensing system according to various embodiments, is discussed below. Then, additional applications of such technology for home health care systems are described in greater detail.

VCA systems may use cameras that are calibrated in order to detect and identify objects. For example, rather than simply detecting an object based on its relative dimensions, which can represent, for example, a shape of pill box or a shape of a human being, calibrated VCA systems are able to detect a shape of an object as well as its real-world size. As a result, the system can more accurately detect certain objects. For example, in a non-calibrated system, a VCA system for counting a number of people that appear in a frame of a video stream may count the shapes of both actual people, and of miniature dolls in the frame as people. Similarly, a non-calibrated system attempting to count a number of pill boxes may count both garbage cans and actual pill boxes as pill boxes. To avoid this sort of error, VCA systems can be calibrated to provide scale and determine the actual sizes (e.g., actual height and width dimensions) of objects, which improves analysis accuracy.

Figure 2:
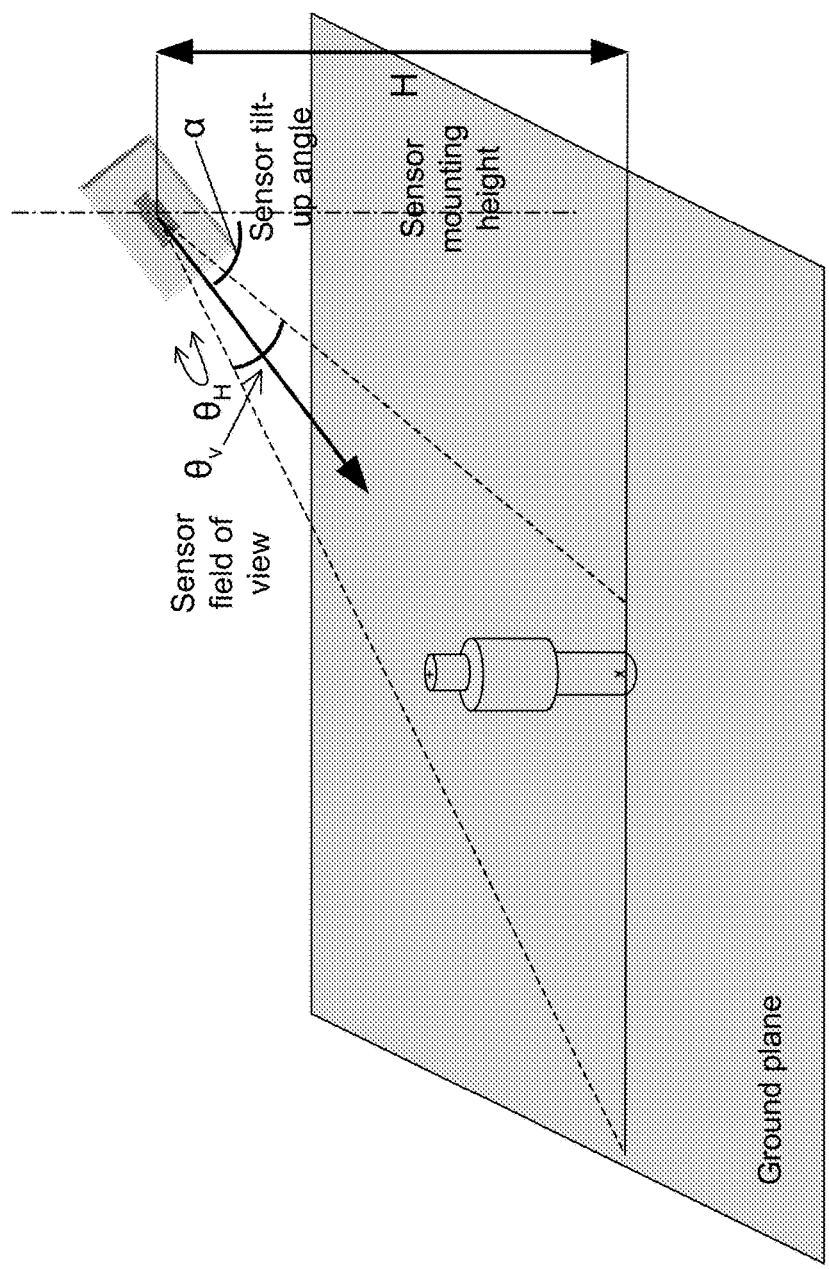
FIG. 2 shows a camera system that can be calibrated to assist in determining the scale and sizes of objects in the field of view, according to one exemplary embodiment.

As one example, FIG. 2 shows a camera system that can be calibrated to assist in determining the scale and sizes of objects in the field of view. To calibrate the camera system, parameters such as camera height (H), vertical and horizontal camera field of view angles ($\theta_H$, $\theta_V$), and camera tilt angle ($\alpha$) can be used. These parameters could be determined by direct measurement, camera specifications, or other calibration processes. For examples of calibration procedures, see the '923 patent, and see also U.S. Pat. No. 7,801,330, issued to Zhang et al. on Sep. 21, 2010, the contents of which are incorporated herein by reference in their entirety. Using these parameters and other information, such as detected outer boundaries of an object (e.g., a top and bottom of a person or box), the camera system can generally determine the real world size and shape of an object for identification purposes.

However, even a calibrated camera system can have some difficulties detecting real-world objects. For example, to determine an actual height of an object, such as a person, a calibrated system may search for the top of the object (e.g., the person's head) and the bottom of the object (e.g., the person's feet). However, part of a person's body, including the feet may be occluded by one or more objects, such as, for example, another person, or a shopping cart. In this case, the system may not be able to detect certain information about the person, such as the person's height. Similarly, if a person is lying down and a calibrated camera system detects the person's feet and head, it may determine a height of the person, but not a height above the floor at which the person is positioned. Therefore, the calibrated camera system may not be able to detect that a person is lying down after performing object detection.

As another example, if a second person is standing behind a first person, even if the system detects the second person, for example, based on an algorithm that detects human heads or faces, the system may not necessarily know the height of the second person. The second person may be taller than the first person and standing very close to the first person, or the second person may be shorter than the first person, but standing further away from the second person. In either case, however, the camera only sees the first person and the second person's head just above the first person.

Another example where a calibrated system may erroneously detect people or other objects is when shadows or reflections are involved, or where people are occluded by immobile objects, such as furniture, for example. A calibrated camera system may see a shadow or reflection, and may determine, erroneously, that it is an actual person, or may see two parts of a person separated by an immobile pole or other obstruction, and may fail to recognize both parts of the person as a single person.

To remedy these problems, particularly in home health care monitoring where patients will often be sitting, lying down, obstructed by furniture, etc., in one embodiment, a depth sensor is used together with the calibration information to help determine the real world height or size of a person or object and therefore to help determine a position of the person or object. The depth sensor information can be used to supplement, or verify information collected or determined by the calibrated camera system, and/or to help determine a position of a detected person or object.

As opposed to inferring distance based on geometric equations, certain depth sensors determine the distance of objects from a sensor device by obtaining a direct measurement. For example, the measurement may be made using an infrared projector and a monochromatic CMOS sensor. An exemplary system for determining depth of objects in a three-dimensional space is described in U.S. Patent Application Publication No. 2010/0199228, to Latta et al., published on Aug. 5, 2010, the contents of which are incorporated herein by reference in their entirety. However, depth determination is not limited to the method disclosed in Latta et al., and depth can be determined based on a plurality of different sources, such as lidar, stereopsis, or structured light, for example.

In one embodiment, depth information can be used to supplement camera image information to determine the identity of certain objects. For example, in one embodiment, camera image information can be used to determine all potential human beings in a camera's field of view. For example, a calibrated camera system may be configured to detect objects that are not part of the background (e.g., moving objects) and that have a shape approximately the same shape as a human being. Depth sensor information can then be used to determine a real-world height or size of each object detected as a potential human being, and as a result, the number and location of actual human beings, as well as their positioning, can be more accurately determined, for example, based on the potential human being objects that are at certain heights or that occupy a certain threshold volume. In another embodiment, the depth sensor information can be used as a filter to count certain groups of people, for example, if only adults are desired to be counted.

Many methods have been proposed on using depth data to perform scene analysis. In U.S. Pat. No. 8,238,607 and U.S. Patent Application Publication No. 2012/0314905, for example, stereo videos are used to generate disparity map and depth map, and human detection and tracking are performed on the computed depth map. In U.S. Pat. No. 7,831,087, "Plan-View" images are generated from both depth data and non-depth data, and object detection is performed on the "Plan-view" images through "Plan-view" templates. In U.S. Pat. No. 8,320,621 and U.S. Patent Application Publication No. 2012/0197393, a new 3D imaging device RGBD sensor is introduced which can provide both RGB and depth components for each pixel on the image. Humans and human body parts are detected and tracked on the depth map. In U.S. Patent Application No. 2005/0201612, stereo images are used to produce a height map, the human objects are detected by detecting heads using connected component analysis on the height map. In U.S. Patent Application Publication No. 2012/0293635, the above RGBD sensor is used to detect the head pose, and the head position and orientation are estimated by tracking head feature points in 3D space.

Most of the prior art performs the object detection and tracking in the depth space or 3D space. This usually results in a lower resolution and lost details on the objects of interest. Further, the accuracy and quality of the depth data is usually not as good as those RGB image data, and methods of how to deal with the noise and incompleteness of the depth data in the scene analysis have not been well addressed. In addition, processing for object detection and tracking using 3D space data for a whole scene can be computationally complex or even prohibitive. In the present application, a way to use aligned depth data to assist in object detection/tracking under the existing non-depth sensor framework is proposed. The approach is based on the existing RGB image sensor based framework, and uses additional depth information to solve or alleviate certain existing problems. The object detection and tracking is still performed on the traditional non-depth 2D image space, and the depth data is used to provide physical location and size information on objects of interest to help the object detection, segmentation, classification and tracking processes. As a result, particularly when used in a home health care environment, a video content analysis system can perform more accurate and reliable event detection, and can monitor patients in a way not previously attainable.

Figure 3A:
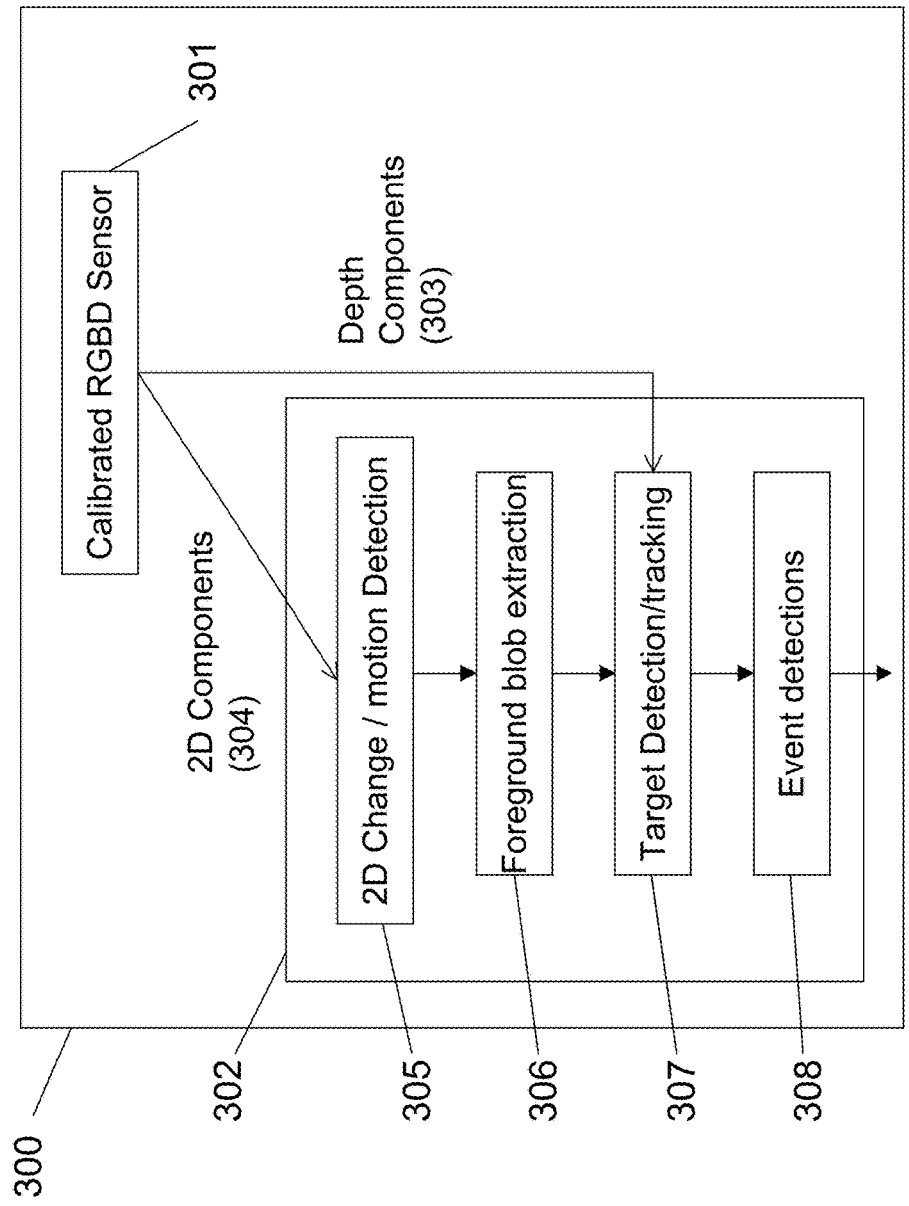
FIG. 3A shows a conceptual block diagram of a video surveillance system and method using one or more sensors that capture two-dimensional (2D) image data and depth data, according to certain exemplary embodiments.

FIG. 3A shows a conceptual block diagram of a video surveillance system 200 and method using, for example, a plurality of RGBD sensors or plurality of other sensors that capture two-dimensional (2D) image data and depth data. In one embodiment, RGBD video frames are captured by and received from a calibrated RGBD sensor 301. Sensor 301 corresponds to one of the cameras shown in FIG. 1. As such, in the home health care environment, a plurality of sensors 301 may be used. For each sensor, for each image pixel of a video frame, the RGB components and the depth component may be determined. The RGB components and the depth component may come from a same device, like the one introduced in U.S. Pat. No. 8,320,621, or from separated devices and computed through additional procedures, for example, by a disparity map from stereo cameras. Although RGB type data is mainly discussed herein, the 2D image data captured by a camera and used in the video content analysis system and method disclosed herein can be other types of color data or other types of 2D data. RGB is used herein merely as an example.

In one embodiment, the RGB components 304 may be processed by existing video content analysis algorithms, such as like described in U.S. Pat. No. 7,825,954, to Zhang et al., published on Nov. 2, 2010, the contents of which are incorporated herein by reference in their entirety. As such, the system may analyze the 2D (e.g., RGB) components 304 to first perform motion and change detection (step 305) to separate foreground from background. For example, in one embodiment, pixels that are detected as moving are indicated to be foreground data (e.g., by being labeled with a logic value, such as "1"), and pixels detected as non-moving are indicated to be background data (e.g., by being labeled with a different logic value, such as "0"). The output of step 305 may include a foreground mask for each frame. Next, the foreground regions may be divided into separate blobs by blob extraction (step 306). During blob extraction, in one embodiment, the individual foreground pixels are grouped spatially. Foreground pixels that are touching or close to each other are assumed to correspond to the same object and are combined into a single blob. As a result, for each frame, one or more blobs may be detected. Each blob or a part of each blob may correspond to one or more targets at each timestamp (where, for example, a particular timestamp may be associated with a frame of the video). In target tracking step 307 targets may be detected based on the blobs extracted in step 306, and each target may be tracked, where each target may correspond to an object in the scene that is desired to be tracked. The depth component 303 is used here to provide a more accurate determination of which blobs correspond to targets, as opposed to, for example, which blobs correspond to objects that are not targets and do not need to be tracked. Additionally, the depth component 303 may be used to better distinguish different targets from each other, or to determine a position of a target.

For example, in one embodiment, a blob may be detected, and depth information may be used to determine its size or volume. Alternatively, or additionally, facial recognition may be applied to the blob. The blob may correspond to a person. Based on the size or volume determination, and/or the facial recognition, the video content analysis system may determine that the blob is a person, and may indicate the person to be a target. Subsequently (or at the same time), the video content analysis system may use the depth information to determine a height of the person or the height of a face of the person where facial recognition is used, and therefore may estimate a position of the person based on the height (e.g., sitting, lying down, standing). This may occur even if part or all of the person's body is occluded, for example, by covers on a bed, or by the back of a chair. The person may be tracked based on changes in position, such as sitting up after lying down, getting out of bed, etc.

Finally, after a target and optional additional information about the target is detected, event detection step 308 performs event detection based on user-defined rules and the targets detected and tracked in step 307. In the embodiments discussed herein, video content analysis can be performed in real-time, or may be performed on video sequences stored previously, for example, by a DVR, NVR or other recording equipment attached to a camera, or in a central computer system In one embodiment, though not shown in FIG. 3A, image data and depth data from a plurality of sensors, or cameras, are analyzed by a video content analysis system, such as 302, or are analyzed by a plurality of separate video content analysis systems (e.g., each camera may have embedded hardware and software to perform at least part of a video content analysis process). Event detection may then be determined based on a collective video content analysis across the plurality of cameras.

As a result of the above steps, the following method may be performed. First, a video sequence that includes a plurality of frames may be captured, for example, by an RGBD sensor, such as a camera having depth detection capabilities. Each frame may include a video image. For each frame, two-dimensional (2D) image data (e.g., RGB data) may be extracted, and also depth data may be extracted. The 2D image data and depth data may then be transmitted to and received by a video content analysis system (e.g., one or more processors executing one or more algorithms for analyzing video content). The 2D image data of the video sequence may then be processed to differentiate foreground data from background data and to detect one or more blobs comprised of the foreground data. The one or more blobs may correspond to one or more real-world objects, and correspond to one or more potential targets. For each detected blob, the depth data may be used to determine whether at least part of the blob corresponds to at least part of a target, or to determine whether to track at least a part of the blob as a target. For example, it may be determined that an entire first blob corresponds to a single real-world object (e.g., single person), and so that the first blob is determined to correspond to a first target. Alternatively, it may be determined that a first blob actually corresponds to two different real-world objects (e.g. two people), and so part of that first blob is determined to correspond to a first target, and another part of the first blob is determined to correspond to a second target. In a third case, a blob may be determined to correspond to only part of a real-world object, and so that blob and an additional blob may collectively be determined to correspond to a single target (e.g., a single person).

After it is determined that at least part of a blob corresponds to at least part of a target, the target is tracked and at least one event associated with the target is detected.

Stated in a different way, as discussed in the examples above, a video sequence may be received that includes a plurality of frames, each frame including a video image. For each frame, image data of the video image and also depth data associated with the video image may be received (e.g., it may be extracted from the video sequence and received by a video content analysis system). The image data may then be analyzed to detect one or more objects depicted in the video sequence (e.g., a blob may be extracted, and the system initially assumes that the blob corresponds to a real-world object in the video sequence, for example, by treating the blob as a potential target). Next, using the depth data along with the one or more detected objects, at least a first object of the one or more detected objects is classified as an object to be tracked. For example the first object may be classified as a person to be tracked, an adult to be tracked, a vehicle to be tracked, etc. The object to be tracked may be treated as a target. Next, tracking is performed on at least the first classified object. For example, based on depth data, a person maybe tracked and it may be determined if the person is lying down, standing up, or sitting. Finally, event detection analysis is performed on the first classified object. In certain embodiments, the video content analysis described above is automatically performed by a computer system, such as a video content analysis system.

In one embodiment, the depth data 303 is mainly used in step 307 to help the target detection and tracking processes. The inputs to step 307 may be foreground image blobs extracted from the video frames based on change and motion detection. Each image blob may include a group of connected foreground pixels representing all or part of a physical object, or multiple physical objects. A correct understanding on what each image blob represents is important for the overall system performance. The disclosed embodiments use the depth data to help make the correct decision in step 307 regarding which targets to track.

Figure 3B:
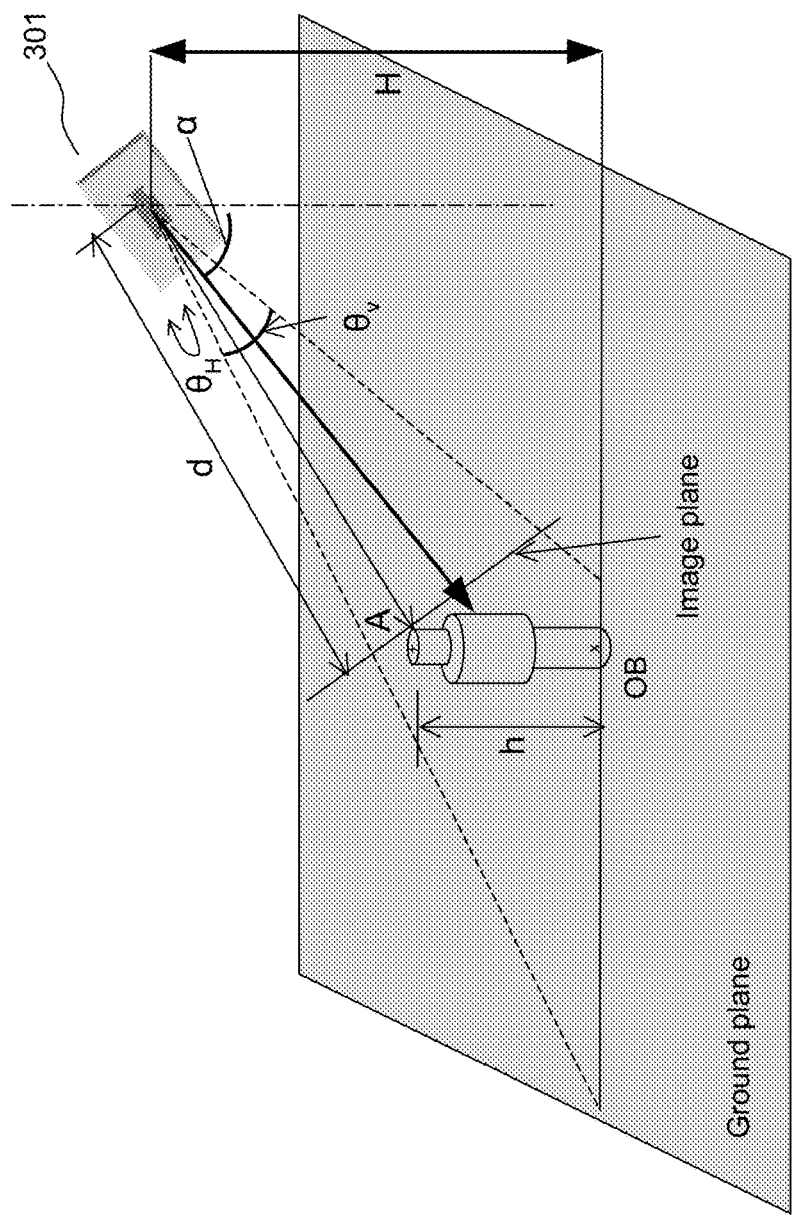
FIG. 3B depicts an example of depth information that can be used in a depth-enhanced video content analysis system, according to certain embodiments.

FIG. 3B depicts one example of depth information that can be used to assist in deciding which targets to track. For example, FIG. 3B shows a camera device 301 mounted at a particular location (e.g., a ceiling). The camera device has a particular height (H), vertical and horizontal camera field of view angles ($\theta_H$, $\theta_V$), and camera tilt angle ($\alpha$). The camera device may include, for example, an image capture portion, such as a standard digital or analog camera, and a depth detection portion, such as an infrared detector as described above, stereo vision technology, or other known devices for directly measuring the depth and distance of objects in a three-dimensional space. In one embodiment, for example, camera device 301 is a calibrated RGBD sensor with a known camera height H, tilt up angle $\alpha$, and image horizontal and vertical field of views (e.g., known field of view angle and known number of pixels in the field of view). In one embodiment, an object (OB) has a particular shape and a height (h). The height may not be initially known based on 2D data alone. To determine the height, a depth map may be created for the pixels that correspond to a detected blob that represents the person. In one embodiment, each pixel of a blob may be associated with a particular three-dimensional real-world coordinate that indicates the actual location of the object or part of the object that the pixel represents. As such, the distance between the camera and each real-world object represented by one or more pixels can be determined, and using the calibration information and the distance, a height of each pixel or each object represented by one or more pixels can be determined.

As shown in FIG. 3B, a three-dimensional coordinate, and thus a real-world height, at point A, which may correspond in one embodiment to the top of a person's head, can be determined by applying geometric equations that include as variables the calibration values (H, $\alpha$, $\theta_H$, and $\theta_V$) and the distance (d), also referred to herein as depth. As a result of the determined height, additional filtering or analysis can be performed. For example, a better determination can be made as to whether the object is actually a person (e.g., as opposed to a shadow, reflection, or animal).

Figure 4A:
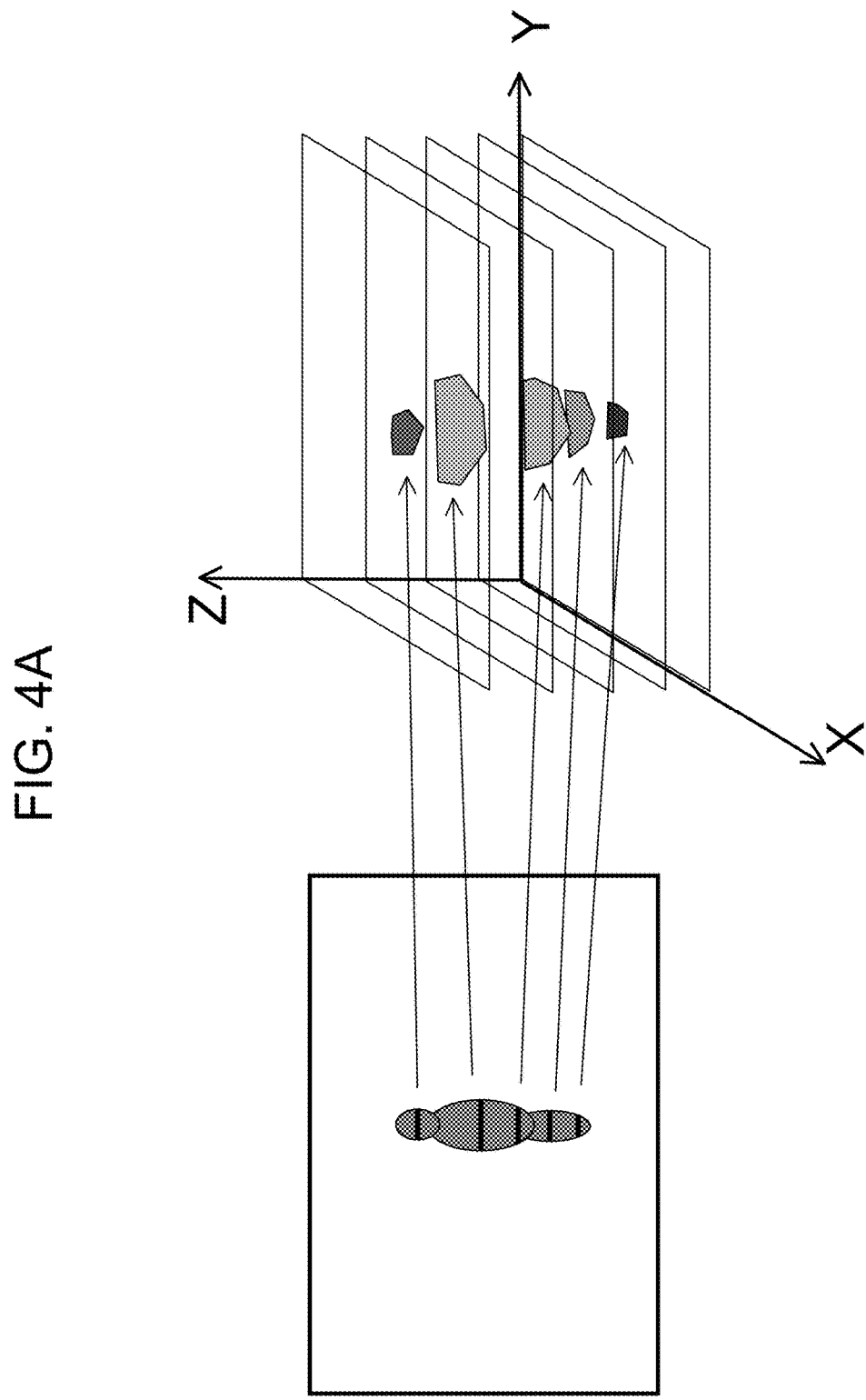
FIG. 4A depicts an exemplary mapping of some samples of image pixels in a blob onto a number of Z-planes in 3D space.

In one embodiment, the physical properties associated with an image blob are estimated by mapping some samples of the image pixels in the blob onto a number of Z-planes in 3D space as illustrated in FIG. 4A. Each Z-plane corresponds to a physical plane parallel to the ground plane. Each point on a Z-plane will have the same physical height in 3D space. The process quantizes the 3D space along the Z axis into a number of 2D planes which are named as Z-planes. The quantization step and the number of Z-planes used may depend on the physical size of the object under investigation. For example, the quantization step can be one foot for human size targets. The quantization step may also depend on some specific requirements of a particular desired detection scheme. For example, if one wants to detect a left behind bag that may be less than one foot in height, a smaller quantization step may be used.

Figure 4B:
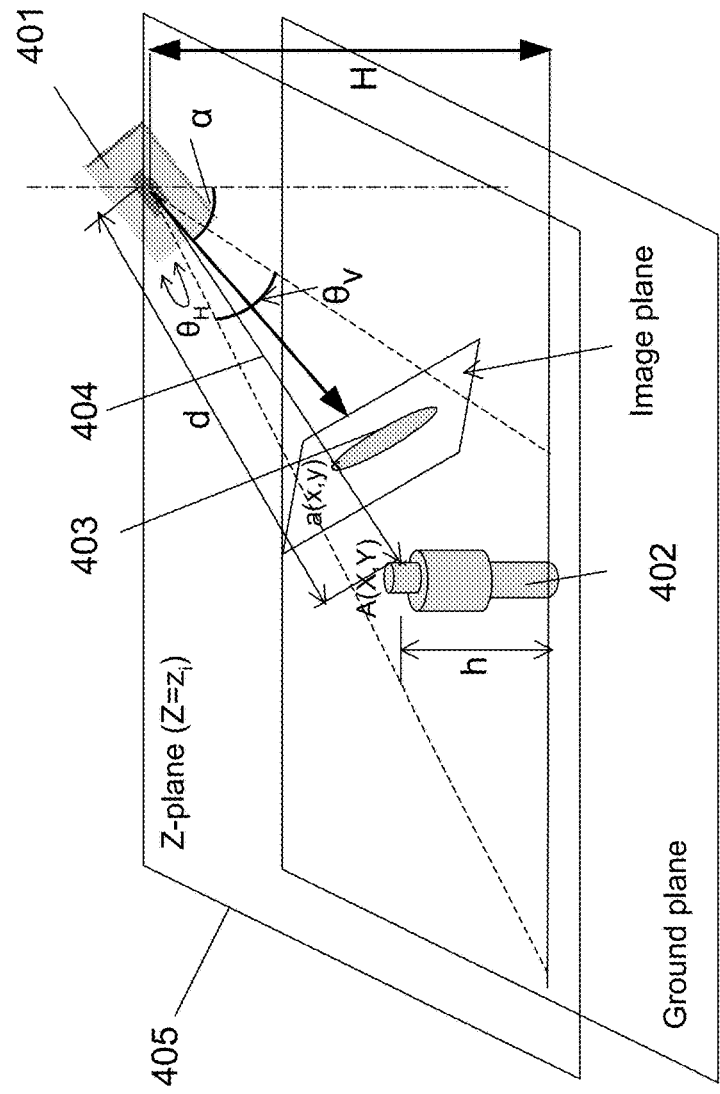
FIG. 4B depicts one example of how to map a pixel in an image blob onto a corresponding Z-plane in physical space, according to one embodiment.

FIG. 4B illustrates one example of how to map a pixel in an image blob onto the corresponding Z-plane in physical space. This mapping method may be implemented using a camera device 401 similar, for example, to that discussed above in connection with FIG. 3. In one embodiment, for example, camera device 401 is a calibrated RGBD sensor with a known camera height H, tilt up angle α, and image horizontal and vertical field of views (e.g., θ$_H$, and θ$_V$). Both the RGB image of video frames and the depth measure for each pixel are provided by the sensor. For example, a human object 402 in the view may be detected as an image blob 403 after step 206 of the method 200 in FIG. 2. For one particular pixel a(x,y) in the image blob 403, the positional direction of the pixel from the camera's point of view 404 can be computed based on its image position (x,y) and the known camera horizontal and vertical field of views. This directional information is then combined with the camera height H, the tilt up angle α, and the pixel depth data d to compute the corresponding 3D location (X, Y, h). Once this 3D location is determined, then the point A(X,Y) can be projected onto the closest Z-plane to the height h. The point A(X,Y) becomes one of the sample points of the blob 403 on that plane (e.g., indicated as the Z$_i$-plane 405 in FIG. 4B).

One advantage of the disclosed embodiments is that not every pixel in the RGB image needs to be mapped onto the Z-planes. For example, in one embodiment, only the foreground pixels that represent the image blobs are to be projected onto the discrete Z-planes, and background pixels do not need to be projected onto Z-planes. In addition, because the number of Z-planes mapped is quantized, not every pixel associated with a blob needs to be projected onto a Z-plane. Further, as described further below, convex hulls may be used to represent the object regions on Z-planes. One convex hull may be approximated by a few pivot points, and not every pixel of a blob in a particular Z-plane needs to be sampled in order to form the convex hull. Thus pixel sampling may be performed for each frame and within each image blob to further reduce the computational complexity. In addition, this approach relies less on the accuracy and completeness of the depth data on every image pixel, and is thus more robust despite inaccuracies that may be associated with the depth information.

The samples on a Z-plane mapped from the corresponding pixels from the same image blob may form different spatial regions on the Z-plane because they may correspond to spatially separated objects. FIG. 5A shows one example of two separate sample groups on a Z-plane. A clustering process may be used to group these Z-plane samples into separate regions as illustrated, for example, in FIG. 5B. In one embodiment, a fast clustering method using the convex hull blob representation is performed. A convex hull may be used to represent each sample cluster. Its convex boundary defines the object blob on the Z-planes. In one embodiment, the physical distance between a sample and an existing sample or cluster is used to perform the clustering.

FIGS. 6A-6C illustrate an example of a definition of the distance between a sample point and an existing, already-determined convex hull region, and the method to compute the distance. In FIG. 6A, 601 is the convex hull of one existing cluster, 602 is the current sample under consideration, if 602 is inside 601, the distance is considered as 0. If the current sample point is outside of an existing cluster, as illustrated in FIGS. 6B and 6C, the closest pivot point may be searched for first, then the current sample point may be projected on to the two boundary lines which contain the closest pivot point. There are two cases in this scenario, as shown in FIGS. 6B and 6C. In FIG. 6B, 603 is the current sample under consideration, 604 is the closest pivot point, 605 and 606 are the two boundary lines containing 604, and 607 and 608 are the two projection points (e.g., each is the closest point between sample point 603 and its respective boundary line 605 or 606). In this case, both projection points are on the extension portions of the lines 605 and 606, not on the actual boundary of the convex region. The distance to the closest pivot point is then used as the distance to the cluster. In FIG. 6C, 609 is the current sample under consideration, 610 is the closest pivot point, and 611 and 612 are the two boundary lines containing 610. In this case, 613 is the projection point of 609 on 612 and it is on the boundary of the convex hull. Thus the distance between 609 and 613 is considered as the distance between the sample point and the existing cluster. As a result of these calculations, the distance between the sample point 603 and the cluster can be thought of as a minimum distance among (1) the distance between the sample point 603 and a closest pivot point, and (2) a shortest distance between the sample point 603 and a convex hull boundary.

A physical distance threshold may be used to determine whether a sample point outside the cluster should belong to the cluster. Thus the clustering process can be described as follows. Given a list of sample points on a Z-plane which are mapped from sample pixels from an image blob, select a first sample and consider it as the first sample cluster. Then iterate through all the remaining sample points. For a given sample point, compute its distance to all the existing blob clusters. If the distance to a cluster is less than a distance threshold predetermined as a parameter, update this cluster by including this sample into the cluster convex hull. If one sample belongs to multiple clusters, merge all the corresponding cluster convex hulls into a new cluster. If a sample does not belong to any existing clusters, create a new cluster using the current sample. The exemplary method is a one-pass clustering process, and the distance computation only involves a limited number of pivot points. As a result, the clustering process, and the resulting target detection and tracking is computationally efficient.

Since a typical RGBD camera is not able to see through an object, a self-occlusion issue often occurs in the 3D space representation of an object. FIG. 7 depicts an exemplary method of addressing this self-occlusion problem. FIG. 7 shows a Z-plane 701 determined based on a camera location 702. The pivot points of an observed convex cluster obtained through the above mapping process are marked as "+". For example, one of these pivot points is indicated as 703. Looking from the camera 702 point of view (wherein the camera is placed a particular distance in the X-Y direction from the object represented by the cluster), 704 is the right most pivot point and 705 is the left most pivot point. These two points are used to determine the self-occlusion line 706. Next, for all the pivot points between the self-occlusion line and the camera, their mirror points on the opposite side of the line 706 are computed and marked as "x", for example, 707 is the mirror point of 703. The final convex cluster 708, is determined by both the original pivot sample points and the mirror sample points. The object self-occlusion is more severe when the camera view is oblique.

In certain embodiments, a camera position may be directly above part of an object, or almost directly above the object. FIG. 8 shows an almost overhead camera view case, where 801 is the Z-plane, and 802 is the projected camera on the Z-plane. Although there is still a self-occlusion line 803, no extra mirror pivot points are generated because the camera 802 is inside a Z-plane blob cluster and is very close to the self-occlusion line. As described above, the self-occlusion line is the line between a left-most and right-most point, so the self-occlusion line may stay the same for the different camera angles, even though different angles may show more or less 2D image data of an upper surface of an object. Thus, the amount of self-occlusion compensation on each Z-plane is adaptive to the camera position and viewing direction, and this compensation process can provide a more accurate measurement on the projected physical size of the object on each Z-plane.

FIG. 9 illustrates an example of an image blob and its projected convex hull slices on a list of corresponding Z-planes. The physical volume of the image blob can be further computed using these convex hull slices on the Z-planes. For a given image blob, assuming there are N Z-planes denoted as $Z_0, Z_1, \ldots, Z_{N-1}$, and on each plane $Z_i$, the corresponding convex hull slice area is $S_i$, then the physical volume of the blob can be estimated as:

$$V = \sum_{i=0}^{N-2} (S_i + S_{i+1}) * (Z_{i+1} - Z_i)/2$$

The physical volume measurement may be used, for example, to perform target filtering and target classification. For example, it can increase the confidence on detecting a human object. A human blob should have a physical volume close to an average physical human. The change of human postures will change the image appearance and height but typically will only have small impact on the human volume. Meanwhile, the human pose change can be detected by tracking the changes of physical height and the projected areas on different Z-planes. The physical height and volume measurements can also be used to distinguishing different types of people from others, such as children from adults.

The physical volume measure may also be used to filter out spurious foreground blobs caused by illumination factors, such as shadows and reflections. These types of non-legitimate blobs usually have little physical volume. The physical height and volume information can be used to detect other types of targets such as vehicles or shopping carts, for example. The physical sizes at different Z-planes are strong cues to detect objects with different physical size and shapes. Just using a height map without volume information may incorrectly detect certain blobs, such as a shadow on a wall, as a person.

Figure 10:
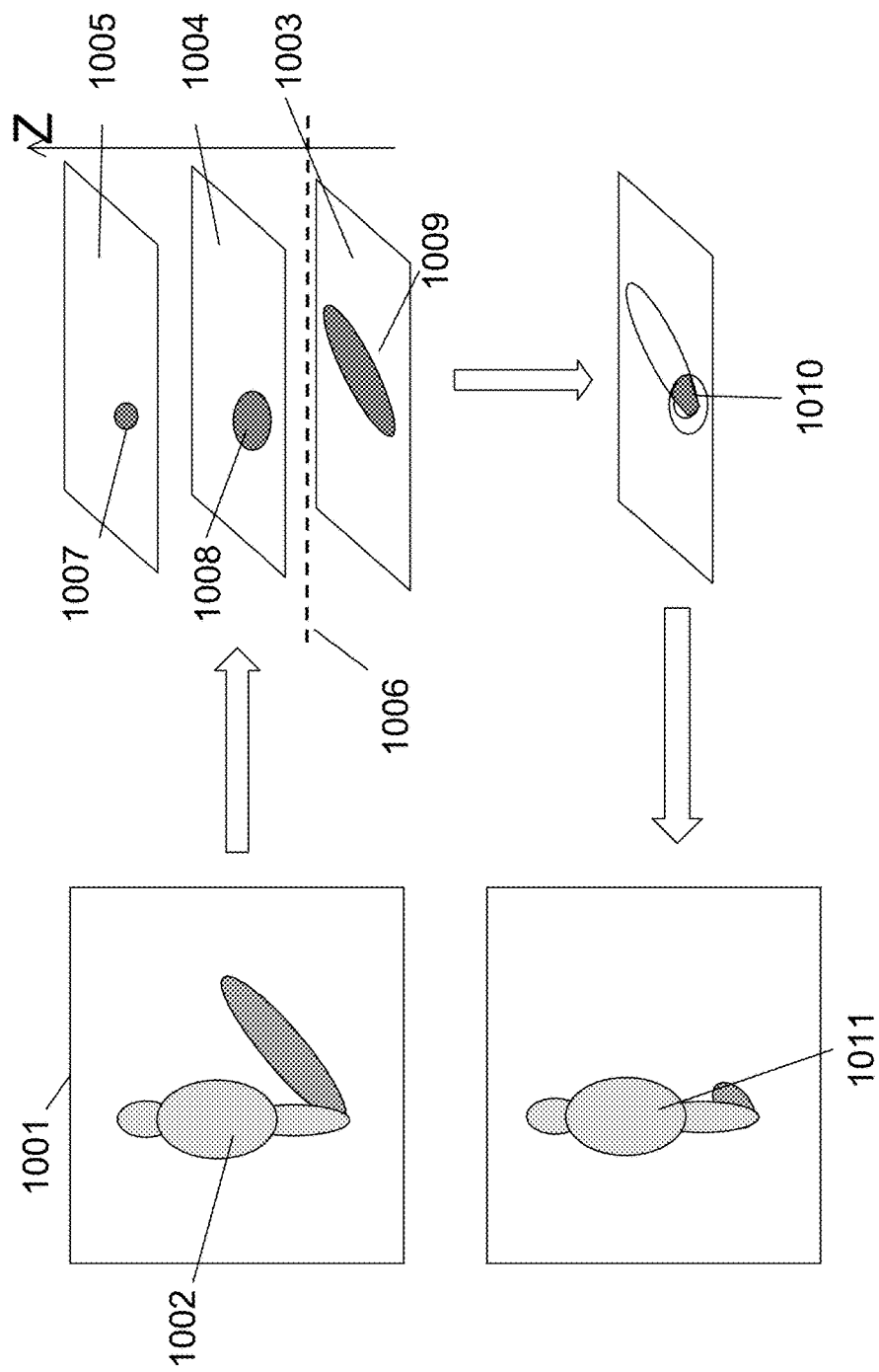
FIG. 10 shows one example of how to remove shadows in an image blob, according to one exemplary embodiment.

FIG. 10 shows one example of how to remove shadows in an image blob. An RGB image 1001 may include a detected foreground image blob 1002, which corresponds to both a human object and its shadow casting on the ground. Without the depth analysis, the system would have difficulty understanding what type of object the blob represents. Therefore, in one embodiment, to remove the impact of shadow, first, the image blob is projected onto a number of Z-planes indicated as 1003, 1004, and 1005. A height threshold 1006 is used separate the Z-planes into ground plane and non-ground planes. Blob slices 1007 and 1008 on the non-ground planes, and blob slice 1009 on the ground plane are determined as blob slices for the blob 1002. The blob slice on the ground plane is likely to be a shadow or reflection. Therefore, to remove the potential shadow and reflection from consideration, the blob slices 1007 and 1008 are projected on to the ground plane, for example, from a top-down view. The projected regions create an overlapping region 1010 with the original ground-plane blob slice 1009. The overlapping region 1010 is then used as the estimated blob slice representing the actual object on the ground plane, instead of the original blob slice 1009. Blob regions 1007, 1008 and 1010 can then be projected back onto the image 1001 to refine the original blob 1002 to appear as blob 1011, where most of the shadow part is ignored. The physical volume of the refined blob 1011 can be also computed using 1007, 1008 and 1010.

Figure 11:
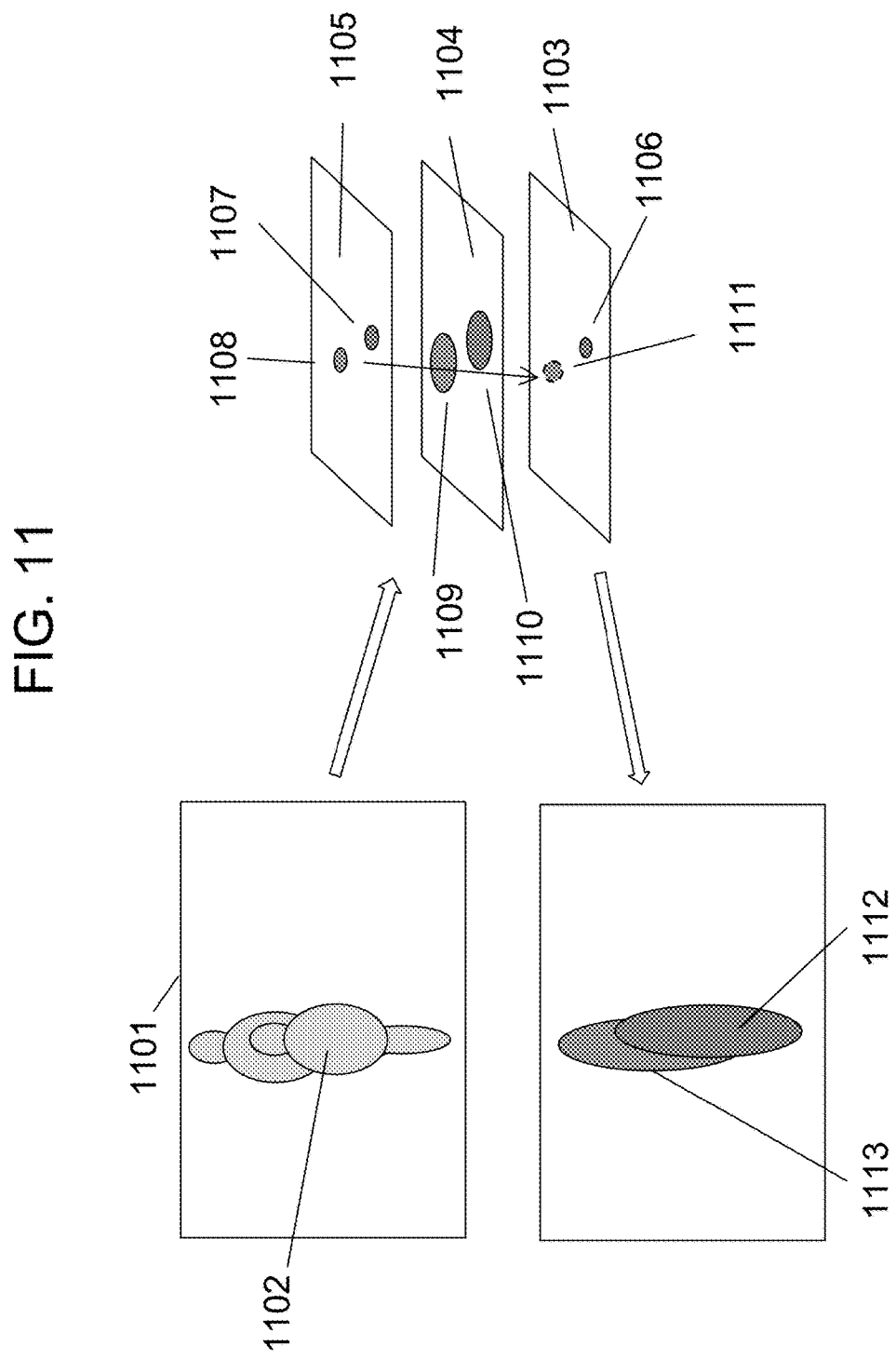
FIG. 11 shows a method of performing blob split on a two-dimensional image using depth information associated with the blob, according to one exemplary embodiment.

Due to the camera viewing perspective, multiple targets not close to one another may be connected in an RGB image and appear as a single blob. In one or more embodiments, they can be separated in the RGB image by using the depth data. FIG. 11 illustrates a method of splitting a single blob of an RGB image corresponding to multiple targets using the depth information associated with the blob. An RGB image 1101 includes a detected foreground image blob 1102, which contains two human targets that are separated in physical space. In the RGB image space, however, these two human objects are connected and it is difficult for the system to understand whether there is a single large human target or there are multiple human targets with occlusions. Though techniques like facial recognition may be used in some cases to resolve this question, in some cases, facial recognition may fail (e.g., if the two people have their backs to the camera). By mapping the image blob on to a list of Z-planes 1103, 1104 and 1105, the system may determine that on some Z-planes 1104 and 1105, the two human objects are separated as they are clustered into different blob regions, indicated by 1107, 1108, 1109 and 1110. This is because in reality, the two objects are separated in space. The depth data is used to separate them out on the Z-planes during the video content analysis. This separation in Z-planes provides strong evidence that the image blob 1102 consists of two human objects instead of one. The separated blob regions on the list of Z-planes are then grouped into two physical objects by checking their spatial overlaps. Those regions whose projected region on the ground plane overlaps with each other may be considered as from the same physical object. For the object (1108, 1109) that does not have a ground plane blob region, the projection from its top plane region 1111 may be used to indicate its ground location. Thus in this example, 1106, 1107, and 1110 correspond to one human object 1112, and 1108, 1109, and 1111 determine another human object 1113 in image 1101. The blob regions of 1112 and 1113 may be obtained by back-projecting their corresponding blob regions on the Z-planes onto the original image. As a result, the physical measurements of the targets represented by the two blobs may be obtained.

Figure 12:
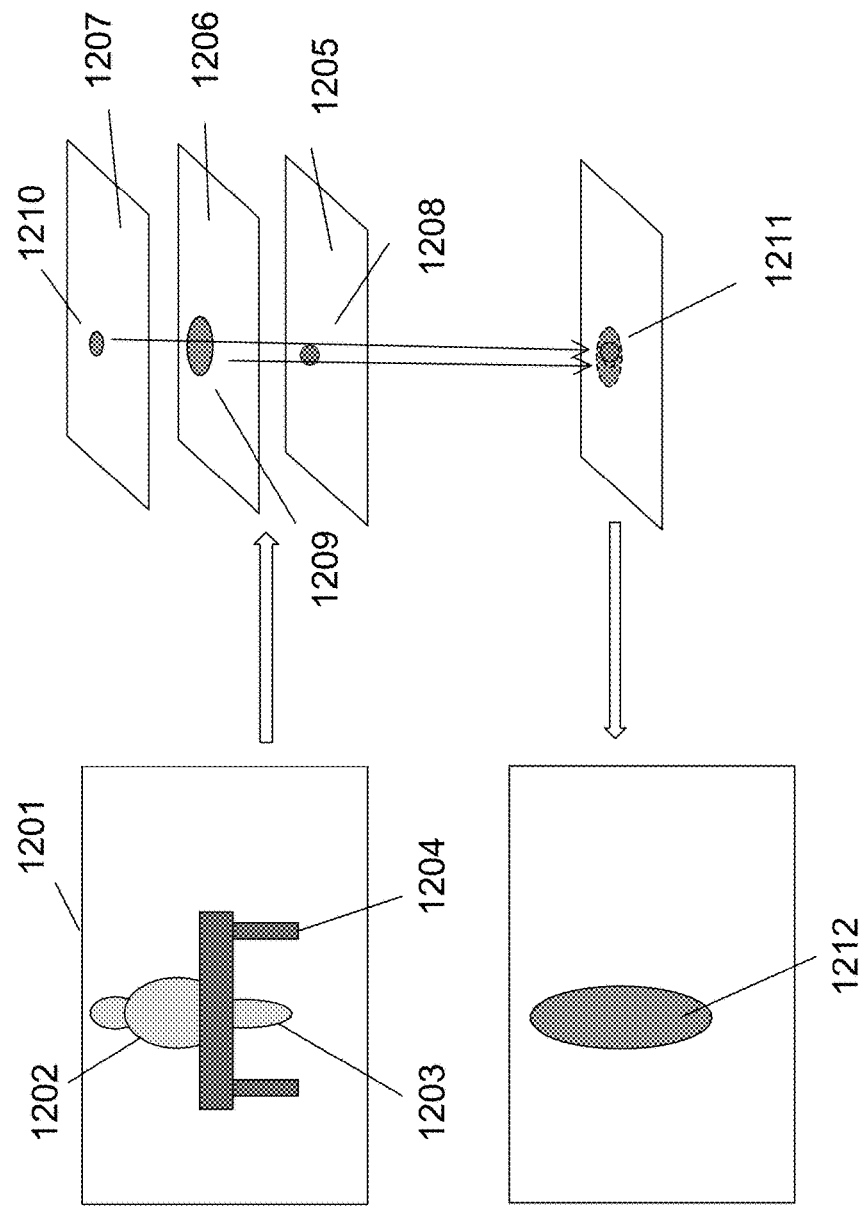
FIG. 12 shows an example of how to merge two falsely separated image blobs, according to one exemplary embodiment.

In some other scenarios, a single foreground object may be occluded by a static background object, or part of the object looks so similar as the background that the system may miss-detect that part as foreground. For example, a person may be occluded by part of a chair or by a bed post. When these happen, the RGB-based system will likely break a single image object into multiple image blobs. This type of problem may also be solved by the depth analysis. FIG. 12 shows an example of how to merge two falsely separated image blobs, according to one embodiment. An RGB image 1201 includes a static background object 1204 which occludes a human object in the scene and causes the system to detect two separated blobs 1202 and 1203. These two image blobs are projected onto the Z-planes 1205, 1206 and 1207. Blob 1203 has a corresponding blob slice 1208 on Z-plane 1205, while blob 1204 has corresponding blob slices 1209 and 1210 on the other two Z-planes. When projecting these blobs onto the ground Z-plane, they all overlap with one another. Further, the physical volume measured by these projected regions on the Z-planes is very close to that of a human object. This provides strong evidence that 1202 and 1203 actually correspond to the same human object. Thus a blob merge operation may be performed in the image 1202 to create a single blob 1212 which can be classified as a target such as an individual human object.

Figure 13:
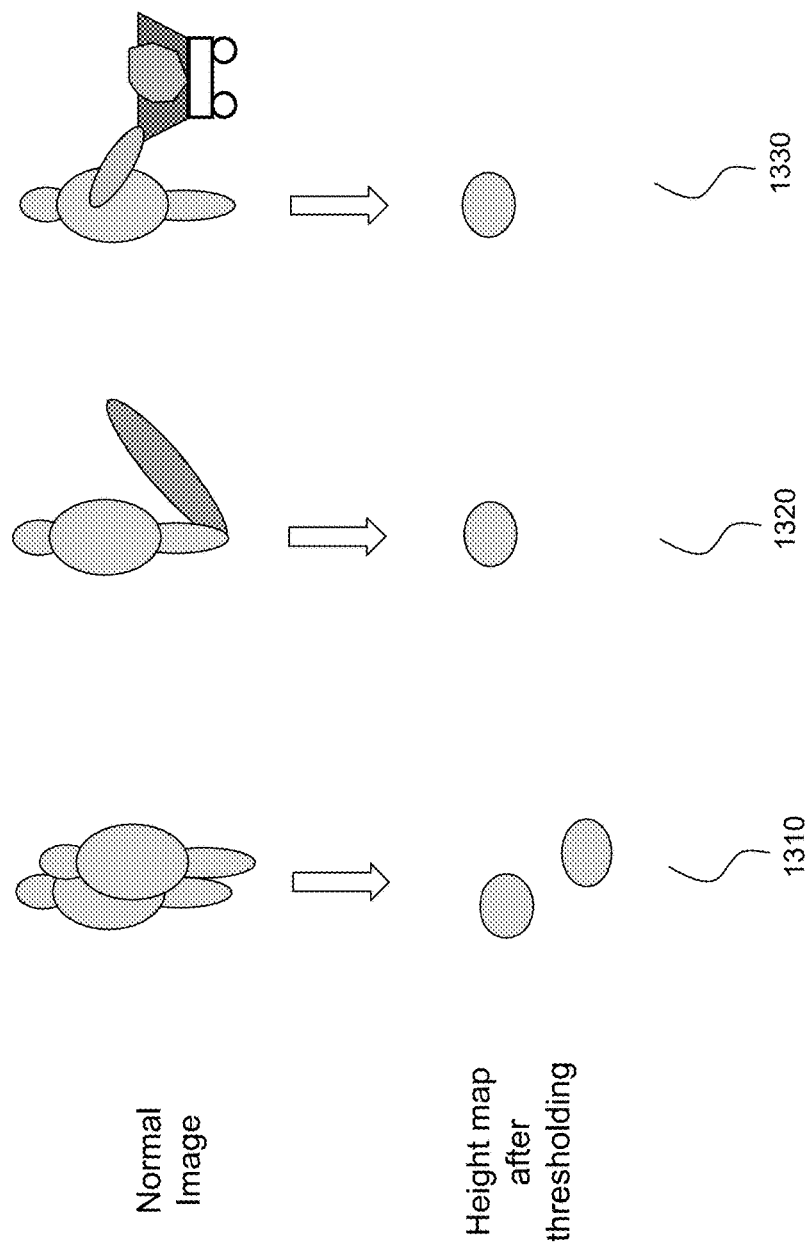
FIG. 13 shows one example of an application of a combined calibration and depth detection system such as described in FIGS. 1-12, according to one embodiment.

One example of a general application of the combined calibration and depth detection system is shown in FIG. 13. As shown in FIG. 13, a height threshold can be applied to detected objects, and can be used to create a target map after the height threshold has been applied. For example, in situation 310, two people stand close together, one occluding part of the other. By applying calibration information and measured depth information to a captured image, a camera device or camera system can determine first that the image is of two targets, and second the height of both targets, and as a result, determines that two people are represented in the captured image. A resulting mapping of the people in the space (a depth map, or height map) can be generated. For example, the mapping may represent a top-down, two-dimensional view of a space, specifically showing the people above a certain height within the space and their location within the two-dimensional view.

In situation 320, however, one person stands in a space, but the person's shadow also appears on the floor. Because the depth detection can be used to remove the effects of the shadow (e.g., as discussed above), the shadow can be omitted from the mapping of people in the space in the depth map. Similarly, in situation 330, one person is partially occluded by a shopping cart, which also has a round object that may be detected as a potential person's head. However, after a height threshold is applied, the round object is assumed to not be a person and is not tracked, and the person is determined to be an actual person and can be tracked. As a result, only one person is included in the mapping of people after the height threshold has been applied. In each of these examples (320 and 330) a vision only person counting system (without depth detection) may have counted two people, thus over-counting the number of people in two of the examples.

After objects are identified as targets, those targets may be tracked within a scene in a video. However, because of the height mapping, the tracking may be analyzed from a top-down, two-dimensional perspective, even though there is no camera capturing images from a top-down view looking directly down at the scene. In one embodiment, a standard Kalman filter can be used to track the location of each object.

Figure 14:
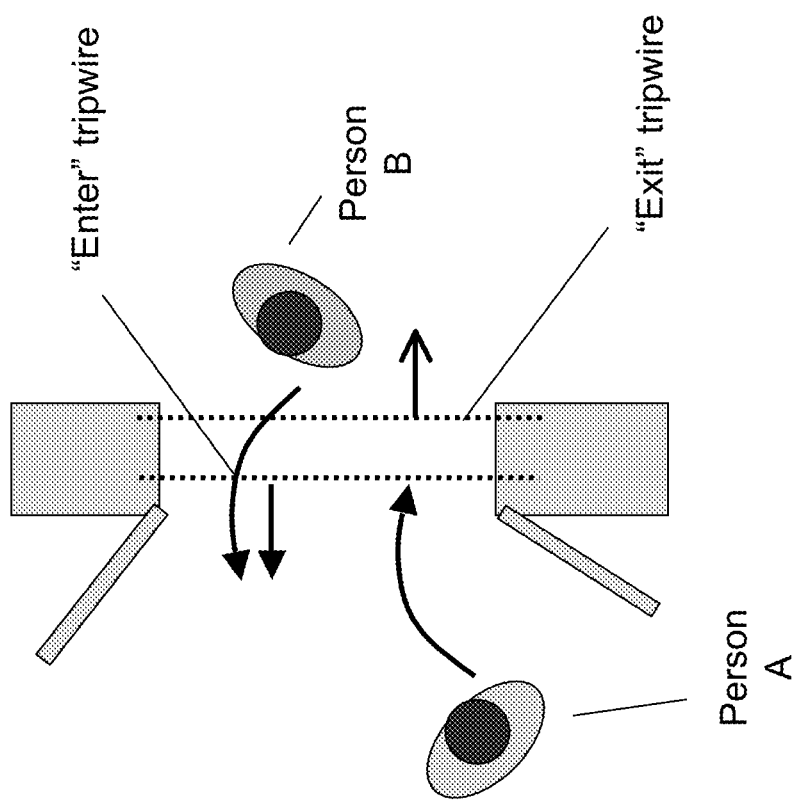
FIG. 14 shows another example of an application of a combined calibration and depth detection system such as described in FIGS. 1-12, according to one embodiment.

Event detection can then be performed based on the detected objects and their tracking information. For example, a virtual tripwire, as described in U.S. Pat. No. 6,696,945, issued to Venetianer et al. on Feb. 24, 2004, the contents of which are incorporated herein by reference in their entirety, can be used to perform counting of one or more people moving in or out of a certain area. An example of a virtual tripwire is shown in FIG. 14. As such, a virtual tripwire may be used in conjunction with the various depth detection techniques described above to count a number of times that a patient enters a kitchen, a bathroom, or another room. This information can be used to detect certain events and to provide improved health care assistance to the patient.

Figure 15:
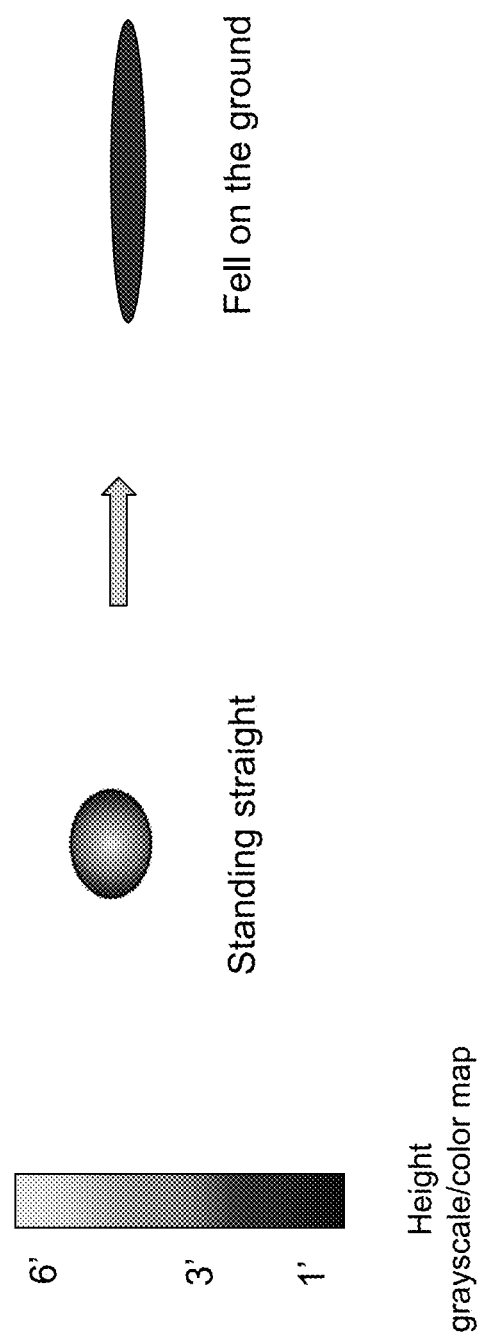
FIG. 15 shows another example of an application of a combined calibration and depth detection system such as described in FIGS. 1-12, according to one embodiment.

Another example of a home health care application of the above embodiments is to perform object tracking to determine when a patient falls down. For example, a captured image may have the shape and size of a person, but the depth information showing that the person's head is near to the ground (e.g., one foot off the ground), may indicate that a person has fallen down or is lying down. One or more alarms can then be triggered based on an event of a person falling being detected. In one embodiment, the person can be mapped into a two-dimensional overhead view as long and narrow, as shown in FIG. 15. In the two-dimensional overhead view, objects can be represented using a color or grayscale scheme that indicates heights of certain objects, in order to show the topography of the objects in the image. As such, a top of someone's head may have a different shade or color from a point lower on the person's head.

Figure 16:
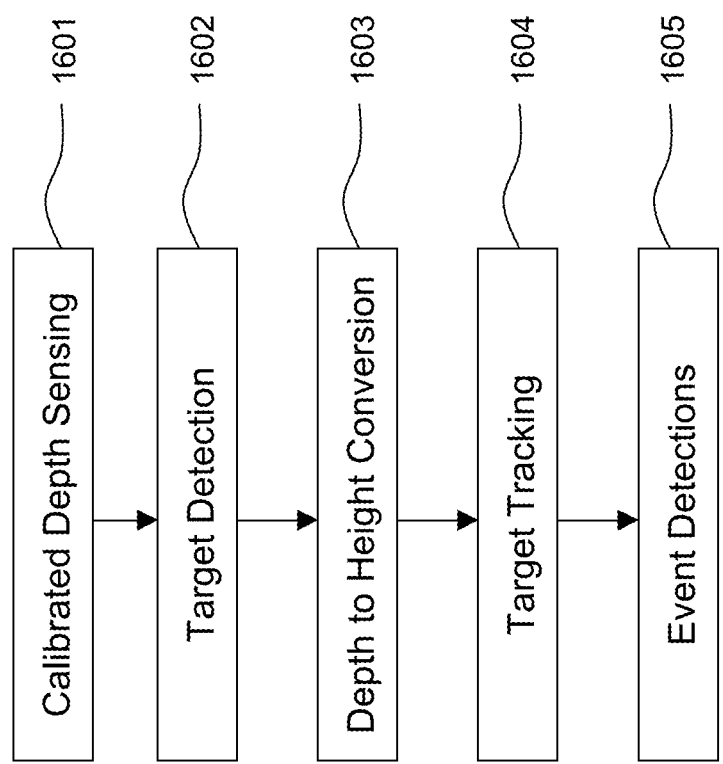
FIG. 16 depicts an exemplary method of performing depth-enhanced video content analysis, according to certain exemplary embodiments.

A method of performing video content analysis (VCA) using the disclosed depth sensing VCA system is shown in FIG. 16. As depicted in FIG. 16, in step 1601, calibrated depth sensing is performed. For example, it may be performed by a camera device that employs an image capture portion and a depth sensor portion to determine a depth of certain objects in the captured image. Based on the depth, and/or other information determined based on the depth of pixels associated with certain objects (e.g., foreground objects), targets in a video sequence may be detected (step 1602). The detected targets can then be converted in step 1603 to a height, to determine the height of the object. The height information can then be used to assist in detecting whether the object is a particular target object, such as for example, a person. For example, an analysis component of the system can determine whether the detected object is above a threshold height, and if so, it can confirm the object as a person to be tracked. In step 1604, the target may be tracked. As a result, in step 1605, events can be determined based on the tracked target. Although certain steps in FIG. 16 are described in a particular order, the steps need not follow in that order. For example, in one embodiment, a height map of foreground objects may be determined prior to detecting targets to be tracked, and based on the height map and a height threshold, only certain targets are then selected to be tracked (e.g., a height map may indicate the heights of foreground objects such as people in the scene, and based on a height threshold such as 4 feet, in one embodiment, only adults are selected as targets to be tracked).

Figure 17:
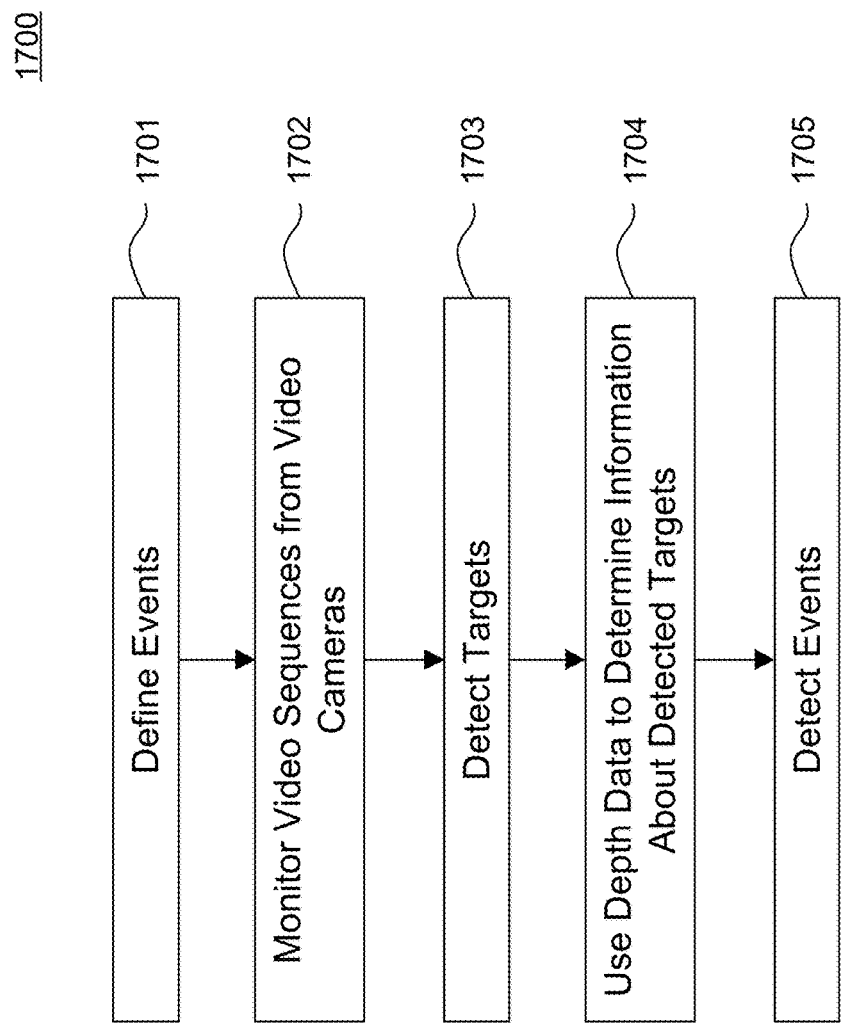
FIG. 17 depicts an exemplary method for performing home health care monitoring using a depth-enhanced video content analysis system, according to certain exemplary embodiments.

FIG. 17 depicts an exemplary method 1700 for performing home health care using a video content analysis system that uses depth sensing, according to certain exemplary embodiments.

As shown in FIG. 17, in order to provide home health care to patients, certain events can be defined (step 1701). The events may be defined by a health care professional who programs them into a computer, for example. The events may be defined according to the needs of a particular patient. The events may be singular events, such as "patient falls," or may be based on collective information, such as "patient spends two hours walking or standing during the day," "patient spends one hour away from home during the day," "patient makes three visits to the bathroom," etc. For example, the following are examples of some events that can be monitored:

Singular Events:
patient falls
patient gets out of bed
patient enters/exits room or house
patient sits up
patient out of bed at 9:00 a.m.
patient walking
patient motionless
Collective Events:
patient spends X hours in bed during Y time period
patient spends X hours lying down during Y time period
patient spends X hours standing up during Y time period
patient spends X hours walking during Y time period
patient visits bathroom Z times during day patient visits kitchen Z times during day
patient does not take any medication during day
patient away from house for X hours during day Many other events can be set. Groups of events can be set, and rules can be set based on the events. Events can be set to include information from different rooms monitored by different cameras in a house. For example, an event of lying down for X hours can be set to correspond to all of the cameras in a house so that whether a patient lies down on a couch or bed, the hours are counted. As discussed below, many of the events are more accurately determined by using depth data along with two-dimensional image data to perform depth-enhanced video content analysis.

Events can be relative to observed or learned patterns. For example, a depth-enhanced video content analysis monitoring system may learn that a patient opens a box, moves his hand toward his mouth, and then drinks a glass of water every morning around 9 a.m. The system may associated these patterns with a "patient takes medications" event. Events can be associated with different people. For example, if an elderly married couple lives in a house, a video content analysis monitoring system can recognize the different people and monitor for certain events based on the person. They can be recognized based on e.g. facial recognition, gender recognition, voice recognition, height, hair, etc. Similarly, if guests are present, they may be differentiated from the monitored people.

Events such as lying down, standing up, sitting, and falling, for example, can be more readily determined using depth data in combination with two-dimensional data, as discussed previously. For example, to detect a person lying in a bed, two-dimensional data of video frame can be analyzed to determine first that a person is in the bed. This may occur based, for example, on shape recognition, face recognition, and/or volume calculations. However, it may not be clear whether the person is lying down or sitting up in the bed. For example, the person's legs may be under the covers, and so only an upper torso and head of the person is detected. The two-dimensional data analysis may not be able to determine whether the torso and head is vertical or horizontal. As such, depth data may be used to determine a height of the person's head, for example. The height of the person's head may then be compared to the height of the bed, to determine whether the person is sitting up or lying down. Another position that may be difficult to distinguish is sitting up versus a person having their knees up.

In step 1702, a plurality of video sequences are monitored from a plurality of video cameras. For example, each of cameras 112, 122, 132, and 142 in FIG. 1 may capture video sequences, two-dimensional image data as well as depth data may be obtained from the video sequences. The data may be obtained by a central computer system (local to the home and/or remote), or may be obtained by processing hardware and software in the cameras themselves.

In step 1703, video content analysis steps are carried out on the two-dimensional image data to detect objects in the video sequences. For example, using analysis techniques such as facial recognition and shape analysis, the objects can be identified as particular targets. For example, a person in the video sequences can be identified as a person, or as a particular patient.

In step 1704, depth data is used to confirm and/or enhance/supplement information about the detected targets. For example, in one embodiment, depth data may be used to determine a height of the target, which in turn can be used to determine a position of the target (e.g., sitting, lying down, standing up). Although step 1703 is depicted as occurring before step 1704, in one embodiment, steps 1703 and 1704 may occur simultaneously, such that two-dimensional analysis is performed in conjunction with depth data confirmation to perform depth-enhanced video content analysis.

In step 1705, based on the information obtained in step 1704, an event may be detected (e.g., patient sits up, patient falls, etc.). A singular event may be detected in a first instance. In addition, a plurality of singular events may be combined to detect a collective event (e.g., person lies down for X hours in a day; person leaves house for X hours during the day, etc.). Based on the events detected, certain rules can be set that trigger alerts or alarms. For example, if a person is detected as lying down for at least X hours in a day (e.g., "person lies down for X hours in a day" event is detected), an alarm may be triggered because this may indicate that the person is having a health-related problem. Different types of and severity levels of alarms can be set based on different types of events.

To implement the system and methods described herein, various computing and optical components may be used, such as one or more of the following: a general purpose computer; supercomputer; a mainframe; a super mini-computer; a mini-computer; a workstation; a micro-computer; a server; an interactive television; a hybrid combination of a computer and an interactive television; a smart phone; a tablet; and application-specific hardware to emulate a computer and/or software. These may include one or more processors, one of more field programmable gate arrays (FPGAs), computer memory, a computer-readable medium such as, for example, any storage device used for storing data accessible by a computer (e.g., a processor may perform various algorithms on data received from a camera device, and a computer memory can then store the information about the various pixels and can store results of blob detection, target detection, and event detection). Examples of a computer-readable medium include: a magnetic hard disk; a floppy disk; an optical disk, such as a CD-ROM and a DVD; a magnetic tape; a memory chip; a solid state storage device; and a carrier wave used to carry computer-readable electronic data, such as those used in transmitting and receiving e-mail or in accessing a network. A tangible computer-readable medium includes computer-readable media, such as listed above, that are physically tangible. In addition, software may be used in combination with the computing and optical components to implement the methods described herein. Software may include rules and/or algorithms to operate a computer, and may include, for example, code segments, instructions, computer programs, and programmed logic. The various computers, cameras, and other image equipment described herein can be connected over a network, which may involve permanent connections such as cables or temporary connections such as those made through telephone or other communication links, and also may include wireless communication links. Examples of a network include: an internet, such as the Internet; an intranet; a local area network (LAN); a wide area network (WAN); and a combination of networks, such as an internet and an intranet. The various hardware and software examples described above are also described in greater detail in the patent documents incorporated by reference herein.

In an exemplary embodiment, depth data and a human model are used to more reliably detect a human arm and its movement. For example, reliable detection of an arm can be used to better detect when a patient reaches for certain items, such as reaching for a medicine cabinet for certain medications. Detecting arm motion only based on monocular vision is error prone, due to shadows, arms or clothing blending into the background, etc. The proposed combined system with the addition of depth and 3D information may significantly improve performance for these applications.

In one embodiment, the depth sensing VCA system can be used to better count and differentiate objects in different groups. For example, the system can use height thresholds to differentiate between adults and children. This may be useful in a home environment, for example, if children visit their grandparents, or if elderly patients have pets, in order to track only the grandparents for health monitoring, and not the children or animals.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present disclosure.

What is claimed is:

1. A method of monitoring the health of a person in a home, the method comprising:
    capturing a video sequence from a first camera disposed within the home, including capturing two-dimensional image data for the video sequence;
    receiving depth data corresponding to the two-dimensional data, and associating the depth data with the video sequence as metadata;
    setting a plurality of events to monitor associated with the person, the events defined to include actions captured from the first camera, at least a first event including the person's body being in a particular bodily position;
    performing video content analysis on the video sequence to determine whether the events have occurred, wherein the video content analysis includes:
        automatically detecting a potential human object from the video sequence based on the two-dimensional image data;
        using the depth data to determine a size, a volume and bodily position of the potential human object, wherein the volume is determined using a plurality of pivot points on a surface of the potential human object, a self-occlusion line, and a corresponding mirror image of each pivot point on the self-occlusion line; and
        based on the size of the potential object, confirming that the potential human object is an actual human, thereby confirming the potential human object as a target; and
    determining that the first event has occurred based on the determined bodily position of the target.

2. The method of claim 1, wherein determining the bodily position of the potential human object includes determining whether the object is standing, sitting, or lying down.

3. The method of claim 1, wherein the first event includes one or more of: (1) a person standing; (2) a person sitting; or (3) a person lying down.

4. The method of claim 3, wherein the first event includes: (1) a person standing for at least a particular amount of time; or (2) a person lying down for at least a particular amount of time.

5. The method of claim 1, further comprising:
    setting an alarm to go off if it is determined that the first event has occurred.

6. A method of monitoring people, the method comprising:
    capturing a video sequence from a first camera disposed in a particular location within a building, including capturing two-dimensional image data;
    receiving depth data for the video sequence, the depth data corresponding to the two-dimensional image data;
    associating the depth data with the video sequence as metadata;
    setting a plurality of events to monitor associated with the people, at least a first event including a person's body being in a particular bodily position;
    performing video content analysis on the video sequence to determine whether the events have occurred, wherein the video content analysis includes:
        (a) automatically detecting a potential human object from the video sequence based on the two-dimensional image data;
        (b) using the depth data to determine a size, a volume and bodily position of the detected potential human object, wherein the volume is determined using a plurality of pivot points on a surface of the potential human object, a self-occlusion line, and a corresponding mirror image of each pivot point on the self-occlusion line; and
        (c) based on the determined size of the detected potential human object, confirming that the detected potential human object is an actual human, thereby confirming the detected potential human object as a target; and
    determining that the first event has occurred based on the determined bodily position of the target.

7. The method of claim 6, wherein the only depth data used during any of the steps (a) through (c) is the depth data for the objects determined to be potential human objects.

8. The method of claim 6, wherein determining the bodily position of the detected potential human object includes determining whether the object is standing, sitting, or lying down.

9. The method of claim 8, wherein the first event includes: (1) a person standing for at least a particular amount of time; or (2) a person lying down for at least a particular amount of time.

10. The method of claim 6, further comprising:
    setting an alarm to go off if it is determined that the first event has occurred.

11. A video surveillance system comprising:
    a first video camera that captures two-dimensional image data and depth data; and
    a video content analysis system configured to:
    receive a video sequence from the first video camera, including receiving two-dimensional image data and depth data for the video sequence;
    associate the depth data with the video sequence as metadata;
    set a plurality of events to monitor associated with people;
    perform video content analysis on the of video sequence to determine whether the events have occurred, wherein the video content analysis includes:
        (a) automatically detecting a potential human object from the video sequence based on the two-dimensional image data;
        (b) using the depth data to determine a size, a volume, and bodily position of the potential human object, wherein the volume is determined using a plurality of pivot points on a surface of the potential human object, a self-occlusion line, and a corresponding mirror image of each pivot point on the self-occlusion line; and (c) based on the size of the potential object, confirming that the potential human object is an actual human, thereby confirming the potential human object as a target; and determining that a first event has occurred based on the determined bodily position of the target.

12. The video surveillance system of claim 11, wherein the only depth data used during any of the steps (a) through (c) is the depth data for the objects determined to be potential human objects.

13. The video surveillance system of claim 11, wherein determining the bodily position of the potential human object includes determining whether the object is standing, sitting, or lying down.

14. The video surveillance system of claim 13, wherein the first event includes: (1) a person standing for at least a particular amount of time; or (2) a person lying down for at least a particular amount of time.

\* \* \* \* \*